(12) United States Patent
Rousseau et al.

(10) Patent No.: US 9,957,495 B2
(45) Date of Patent: May 1, 2018

(54) MEANS AND METHODS FOR GENERATING IMPROVED PROTEINS

(71) Applicants: VIB VZW, Ghent (BE); KATHOLIEKE UNIVERSITEIT LEUVEN, K.U.LEUVEN R&D, Leuven (BE)

(72) Inventors: Frederic Rousseau, Groot-Bijgaarden (BE); Joost Schymkowitz, Meensel-Kiezegem (BE); Ashok Ganesan, Tiruvannamalai (IN); Aleksandra Siekierska, Brussels (BE); Frederik De Smet, Winksele (BE); Joost Van Durme, Wakken (BE)

(73) Assignees: VIB VZW, Ghent (BE); KATHOLIEKE UNIVERSITEIT LEUVEN, K.U. LEUVEN R&D, Leuven (BE)

( * ) Notice: Subject to any disclaimer, the term of this patent is extended or adjusted under 35 U.S.C. 154(b) by 554 days.

(21) Appl. No.: 14/395,049

(22) PCT Filed: Apr. 18, 2013

(86) PCT No.: PCT/EP2013/058052
§ 371 (c)(1),
(2) Date: Oct. 16, 2014

(87) PCT Pub. No.: WO2013/156552
PCT Pub. Date: Oct. 24, 2013

(65) Prior Publication Data
US 2015/0079066 A1 Mar. 19, 2015

Related U.S. Application Data

(60) Provisional application No. 61/635,208, filed on Apr. 18, 2012.

(51) Int. Cl.
| | |
|---|---|
| *C12N 9/24* | (2006.01) |
| *C07K 14/43* | (2006.01) |
| *G06F 19/16* | (2011.01) |
| *C07K 14/32* | (2006.01) |
| *C40B 30/02* | (2006.01) |
| *C12N 9/40* | (2006.01) |
| *C07K 14/435* | (2006.01) |

(52) U.S. Cl.
CPC ............ *C12N 9/2465* (2013.01); *C07K 14/32* (2013.01); *C07K 14/43595* (2013.01); *C40B 30/02* (2013.01); *G06F 19/16* (2013.01)

(58) Field of Classification Search
None
See application file for complete search history.

(56) References Cited

FOREIGN PATENT DOCUMENTS

| WO | 2004066168 A1 | 8/2004 |
|---|---|---|
| WO | 2013156552 A1 | 10/2013 |

OTHER PUBLICATIONS

Reumers et al. ("Protein Sequences Encode Safeguards Against Aggregation" Human Mutation, vol. 30, No. 3, pp. 431-437, Mar. 2009, supplementary materials).*
Schymkowitz et al. (The FoldX web server: an online force field, Nucleic Acids Research, 2005, vol. 33, Web Server issue).*
PDB database result for "acylphosphatase" (retrieved from the Internet: <<http://www.rcsb.org/pdb/results/results.do?tabtoshow=Current&grid=E15DD680>>, retrieved on Sep. 12, 2017).*
Agrawal, N. J. et al., Aggregation in Protein-Based Biotherapeutics: Computational Studies and Tools to Identify Aggregation-Prone Regions, J. of Pharmaceutical Sciences, vol. 100, No. 12, pp. 5081-5095, Dec. 2011.
Beerten, J. et al., "Aggregation gatekeepers modulate protein homeostasis of aggregating sequences and affect bacterial fitness," vol. 25, No. , pp. 357-366, Jun. 2012.
Beerten, J. et al., "Aggregation prone regions and gatekeeping residues in protein sequences," Current Topics in Medicinal Chemistry, vol. 12, No. 22, pp. 2470-2478, Nov. 2012.
Chennamsetty, N. et al., "Aggregation-Prone Motifs in Human Immunoglobulin G" J. Molecular Biology, vol. 391, No. 2, pp. 404-413, Aug. 2009.
Chennamsetty, N. et al, "Design of therapeutic proteins with enhanced stability," vol. 106, No. 29, pp. 11937-11942, Jul. 2009.
Chennamsetty, N. et al., Prediction of Aggregation Prone Regions of Therapeutic Proteins, J. Phys. Chem. B, vol. 114, No. 19, pp. 6614-6624, May 2010.
International Search Report for International Application No. PCT/EP2013/058052, dated Jun. 18, 2013, 6 pages.
Reumers, J. et al., "Protein Sequences Encode Safeguards Against Aggregation" Human Mutation, vol. 30, No. 3, pp. 431-437, Mar. 2009.
Siekierska, A. et al, "αGalactosidase Aggregation Is a Determinant of Pharmacological Chaperone Efficacy on Fabry Disease Mutants," J. of Biological Chemistry, vol. 287, No. 34, pp. 28386-28397, Jul. 2012.
Xu, Jie et al., "Gain of function of mutant p53 by coaggregation with multiple tumor suppressors," Nature Chemical Biology, vol. 7, No. 5, pp. 285-295, May 2011.

* cited by examiner

*Primary Examiner* — Suzanne M Noakes
*Assistant Examiner* — Jae W Lee
(74) *Attorney, Agent, or Firm* — TraskBritt, P.C.

(57) ABSTRACT

The disclosure provides a general method for the production of protein variants with a reduced aggregation propensity without affecting the thermodynamic stability of the variant with respect to the wild-type protein.

2 Claims, 13 Drawing Sheets
(7 of 13 Drawing Sheet(s) Filed in Color)

SEQUENCE LISTING

```
<160> NUMBER OF SEQ ID NOS: 5

<210> SEQ ID NO 1
<211> LENGTH: 429
<212> TYPE: PRT
<213> ORGANISM: Homo sapiens

<400> SEQUENCE: 1

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
```

```
                        245                 250                 255
Ala Gly Pro Gly Gly Trp Asn Asp Pro Asp Met Leu Val Ile Gly Asn
                260                 265                 270

Phe Gly Leu Ser Trp Asn Gln Gln Val Thr Gln Met Ala Leu Trp Ala
            275                 280                 285

Ile Met Ala Ala Pro Leu Phe Met Ser Asn Asp Leu Arg His Ile Ser
290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425

<210> SEQ ID NO 2
<211> LENGTH: 239
<212> TYPE: PRT
<213> ORGANISM: Homo sapiens

<400> SEQUENCE: 2

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Met Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190
```

```
Pro Val Leu Leu Pro Asp Asn His Tyr Leu Ser Tyr Gln Ser Lys Leu
            195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 3
<211> LENGTH: 764
<212> TYPE: PRT
<213> ORGANISM: Bacillus anthracis

<400> SEQUENCE: 3

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Lys Lys Arg Ser Thr Ser Ala Gly Pro Thr Val Pro Asp Arg Asp
        195                 200                 205

Asn Asp Gly Ile Pro Asp Ser Leu Glu Val Glu Gly Tyr Thr Val Asp
    210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285

Pro Ile Val His Val Asp Met Glu Asn Ile Ile Leu Ser Lys Asn Glu
    290                 295                 300

Asp Gln Ser Thr Gln Asn Thr Asp Ser Gln Thr Arg Thr Ile Ser Lys
305                 310                 315                 320

Asn Thr Ser Thr Ser Arg Thr His Thr Ser Glu Val His Gly Asn Ala
                325                 330                 335
```

```
Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
            355                 360                 365

Leu Ala Gly Glu Arg Thr Trp Ala Glu Thr Met Gly Leu Asn Thr Ala
            370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
            405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
            435                 440                 445

Ala Leu Asn Ala Gln Asp Asp Phe Ser Ser Thr Pro Ile Thr Met Asn
            450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
            485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
            515                 520                 525

Leu Val Glu Arg Arg Ile Ala Ala Val Asn Pro Ser Asp Pro Leu Glu
            530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
            565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
            595                 600                 605

Lys Ile Lys Leu Asn Ala Lys Met Asn Ile Leu Ile Arg Asp Lys Arg
            610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
            645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
            675                 680                 685

Tyr Asp Met Leu Asn Ile Ser Ser Leu Arg Gln Asp Gly Lys Thr Phe
            690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
            725                 730                 735

Ile Asn Pro Ser Glu Asn Gly Asp Thr Ser Thr Asn Gly Ile Lys Lys
            740                 745                 750
```

```
Ile Leu Ile Phe Ser Lys Lys Gly Tyr Glu Ile Gly
        755                 760

<210> SEQ ID NO 4
<211> LENGTH: 13
<212> TYPE: PRT
<213> ORGANISM: Artificial Sequence
<220> FEATURE:
<223> OTHER INFORMATION: Sequence comprising Tango zone

<400> SEQUENCE: 4

Asn Ala Thr Asn Ile Tyr Thr Val Leu Asp Lys Ile Lys
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Hsp70 binding sequence

<400> SEQUENCE: 5

Leu Leu Arg Leu Thr Gly Trp
1               5
```

MEANS AND METHODS FOR GENERATING IMPROVED PROTEINS

CROSS-REFERENCE TO RELATED APPLICATIONS

This application is a national phase entry under 35 U.S.C. § 371 of International Patent Application PCT/EP2013/058052, filed Apr. 18, 2013, designating the United States of America and published in English as International Patent Publication WO 2013/156552 A1 on Oct. 24, 2013, which claims the benefit under Article 8 of the Patent Cooperation Treaty and under 35 U.S.C. § 119(e) to U.S. Provisional Patent Application Ser. No. 61/635,208, filed Apr. 18, 2012.

TECHNICAL FIELD

The disclosure relates to the field of protein design and, more particularly, to methods to improve the design of recombinant proteins. Even more particularly, the disclosure provides a method for generating variants of existing proteins that have a reduced protein aggregation.

BACKGROUND

Protein aggregation is mediated by short aggregation-prone sequences that assemble into intermolecular beta-structures, which form the core of the aggregate. In native conditions, these stretches are buried inside the globular structure of the protein and are, hence, protected from aggregation by the thermodynamic stability of the fold. Although the vast majority of proteins contain at least one such aggregation-prone region, protein aggregation in healthy cells is effectively suppressed by a number of mechanisms, which cooperate to maintain proteostasis (Balch, Morimoto et al. 2008). One of them are gatekeeper residues, strongly enriched at the flanks of the aggregating regions, that slow down the aggregation reaction (Otzen, Kristensen et al. 2000; Richardson and Richardson 2002; Rousseau, Serrano et al. 2006; Monsellier and Chiti 2007). Moreover, molecular chaperones, such as Hsp70, bind to exposed aggregating regions, preventing intermolecular assembly to nucleate (Van Durme, Maurer-Stroh et al. 2009). Finally, protein turnover rates (De Baets, Reumers et al. 2011) and protein expression levels (Tartaglia, Pechmann et al. 2009) are tuned to minimize problems with protein aggregation. During normal ageing, these cellular defense mechanisms have been shown to erode (Kikis, Gidalevitz et al. 2010) and many proteins have been observed to break through the proteostasis boundary in ageing tissues (Lee, Weindruch et al. 2000; Zou, Meadows et al. 2000; Lund, Tedesco et al. 2002; Pletcher, Macdonald et al. 2002; Lu, Pan et al. 2004; Ben-Zvi, Miller et al. 2009; Bishop, Lu et al. 2010), often without apparent adverse effects. On the other hand, aggregation of specific proteins has been convincingly linked to a number of age-related human diseases, including neurodegenerative disorders such as Alzheimer Disease and Parkinson Disease, as well as cancer (Xu, Reumers et al. 2011) and metabolic diseases (Ishii, Kase et al. 1996; Soong, Brender et al. 2009). In these cases, the aggregation problem is often exacerbated through mutations, which increase the solvent exposure of the aggregation-prone regions by thermodynamically destabilizing the native structure (Dobson 2004).

However, when proteins are employed for research, therapy or industrial applications, they need to withstand artificial conditions for which evolution has poorly equipped them. Given the ubiquitous nature of aggregation-prone sequences in the proteome, it is not surprising that protein aggregation is often observed when proteins are expressed far beyond their normal concentration in conditions with insufficient or no molecular chaperones. Moreover, once purified, the proteins are expected to last far beyond their natural lifetime, allowing the critical nucleating events to start the protein aggregation reaction. Several methods have been developed to reduce the aggregation problem, for example, by using cell lines with increased chaperone content (Schlieker, Bukau et al. 2002), by generating fusion proteins with solubilizing tags (Zhang, Howitt et al. 2004; Park, Han et al. 2008; Song, Lee et al. 2011), or by careful formulation of buffers (Wang 1999). Another approach would be to adapt the primary sequence to the new requirements through carefully selected mutations. Although this approach has the disadvantage of altering the protein sequence, this is often not a prohibitive consideration.

SUMMARY OF THE DISCLOSURE

In the disclosure, a rational design strategy, designated the SolubiS method, was developed that produces reduced aggregating variants of proteins by simultaneously reducing the aggregation tendency of the variant and at the same time preserving the thermodynamic stability and structural integrity. In exemplary embodiments, the method employs the FoldX (Schymkowitz, Borg et al. 2005) and TANGO (Fernandez-Escamilla, Rousseau et al. 2004) algorithms to identify selected mutations that render a protein less aggregation-prone, while maintaining or even improving its intrinsic stability and function. Specific examples are presented for the generation of variant proteins of industrial utility.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A: Human α-Gal is a homodimer (PDB 3gxp) (J. Lieberman, J. D'Aquino et al. 2009) in which each monomer contains a (β/α)8 domain (central part, yellow and green), where the active site is located and an antiparallel β domain (central part, orange and blue). The structure was visualized with YASARA (Krieger, Koraimann et al. 2002). FIG. 1B: The intrinsic aggregation propensity of the α-Gal sequence as predicted by the TANGO algorithm reveals three strongly aggregation-prone regions: (1) $M_{284}ALWAIMA_{291}$ (SEQ ID NO: 1, residues 281-291), (2) $L_{347}AWAVAMI_{355}$ (SEQ ID NO: 1, residues 347-355) and (3) $Y_{365}TIAVAS_{371}$ (SEQ ID NO: 1, residues 365-371). The regions predicted by TANGO were indicated in the structure with numbers 1, 2 and 3 and were colored in red (FIG. 1A), FIG. 1C: Scatter plots representing the results of computational gatekeeper scans for each of the aggregation-prone regions of α-Gal (ΔΔG FoldX versus ΔTANGO). For the TANGO region 2 mutation, A348R could be identified (green amino acid residue in FIG. 1A), whereas for the TANGO region 3 mutations, A368R and A368P could be identified (green amino acid residue in FIG. 1A), FIG. 1D: A table representing the mutations with a predicted beneficial effect on thermodynamic stability of greater than 2 kcal/mol obtained by FoldX analysis (yellow amino acid residue in FIG. 1A).

FIG. 2A: Western blot of size exclusion chromatography fractions (SEC) of wild-type α-Gal, selected aggregating mutants and improving mutants in transiently transfected Hela cells. WT α-Gal and single improving mutants eluted in later fractions (12.5-14.5 ml) than the aggregating mutants, corresponding to the active soluble form of the protein. FIG. 2B: Quantification of the solubility of α-Gal mutants in transiently transfected Hela cells. The band densities from Western blot of SEC fractions from several experiments were quantified. Fractions from 6.5-10.5 ml elution were considered as insoluble, whereas, from 12.5-14.5 ml, as soluble. Wild-type α-Gal showed approximately 70% of solubility, whereas aggregating mutants were highly insoluble. Single improving mutants reached around 80-90% of total solubility (with the exception of A368R mutant). Statistical significance was calculated in comparison to wild-type α-Gal and means "*" $p<0.05$ and "****" $p<0.0001$. FIG. 2C: Quantification of the enzymatic activity of wild-type α-Gal and single improving mutations in transiently transfected Hela cells. The activity of the wild-type and the mutants was comparably similar with a slight reduction in the case of A368R mutant. FIG. 2D: A scatter plot of the predicted change of the thermodynamic stability ($\Delta\Delta G$ FoldX) associated with the improving mutations versus the experimental values of enzyme activity. For all of the mutations, there is a good correlation between predicted and experimental values.

FIG. 3A: Western blot of size exclusion chromatography fractions (SEC) of wild-type α-Gal and double and triple improving mutants in transiently transfected Hela cells. WT α-Gal and improving mutants eluted in later fractions (12.5-14.5 ml) corresponding to the active soluble form of the protein. FIG. 3B: Quantification of the solubility of α-Gal mutants in transiently transfected Hela cells. The band densities from Western blot of SEC fractions from several experiments were quantified. Fractions from 6.5-10.5 ml elution were considered as insoluble, whereas, from 12.5-14.5 ml, as soluble. Wild-type α-Gal and improving mutants showed similar activity reaching from 70% to 90% of total solubility. FIG. 3C: Quantification of the enzymatic activity of wild-type α-Gal and double and triple improving mutations in transiently transfected Hela cells. The activity of the improved mutants was approximately two-fold higher than the wild-type protein. Statistically significant values in comparison to wild-type were indicated with asterisks: "*" $p<0.001$ and "**" $p<0.0001$. FIG. 3D: Western blot of the expression level of wild-type α-Gal and improved mutants in transiently transfected HeLa cells. All the improving mutants expressed significantly higher than the wild-type α-Gal. This unequal expression of the constructs explains the differences in the enzymatic activity between the constructs.

FIG. 4A: A beta-barrel fold, in which center a chromophore is localized, represents the structure of YFP. FIG. 4B: The intrinsic aggregation propensity of YFP predicted by the TANGO algorithm showed three strongly aggregation-prone regions. The regions predicted by TANGO were indicated in the structure with numbers 1, 2 and 3 and colored in red (FIG. 4A). FIG. 4C: Scatter plots representing the results of computational gatekeeper scans for each of the aggregation-prone regions of YFP ($\Delta\Delta G$ FoldX versus $\Delta$TANGO). For the TANGO region 2, mutations Y151E, M153K and A154P were identified (green amino acid residues in FIG. 4A), whereas for the TANGO region 3, T225E and A227D were identified (green amino acid residues in FIG. 4A).

FIG. 5: A model for troublesome fusion proteins based on YFP. (Panel A) Our model for aggregating fusion proteins that was established by fusing to N terminus of YFP an aggregating peptide LLRLTGW (SEQ ID NO:5) (SS7-YFP). (Panel B) Images of wild-type YFP, SS7-YFP and SS7-YFP Y151E transiently expressed in Hela cells. YFP was equally distributed in the whole cell, whereas SS7-YFP formed bright aggregates (highlighted with red arrows in the image) in the cytoplasm. SolubiS mutant SS7-YFP Y151E, similarly to WT YFP, was evenly distributed in the whole cell and the aggregates formation was significantly reduced as compared to SS7-YFP. The nuclei were visualized with DAPI.

FIG. 6A: A bar chart showing the effect of the improving mutations on the aggregation rate in transiently transfected Hela cells. SS7-YFP expression resulted with aggregation in 50% of cells with the baseline aggregation of YFP on 10% level. Mutation Y151E completely abrogated the aggregation of SS7-YFP model construct. Mutation M153K did not have any effect on the aggregation level, whereas A154P mutant affected the chromophore center, resulting in poor construct expression. Mutations T225E and A227D significantly reduced the aggregation to level 35% and 38%, respectively, and in combination to 30%. Combining single mutations from second regions with single mutations from third region gave a significant reducing effect from 35% (mutants M153K/A227D and A154P/A227D) up to 44% (mutants M153K/T225E and A154P/T225E). Asterisks over the error bars indicating the p-value mean: "*" $p<0.05$, "" $p<0.01$, "*" $p<0.001$ and "****" $p<0.0001$. FIG. 6B: A bar chart showing the effect of the improving mutations on the aggregation rate in transiently transfected U2OS cells. SS7-YFP model construct aggregated in 65% and YFP alone in 16% examined cells. The highest significant reduction of the aggregation level was observed in the case of Y151E mutant. Mutation M153K had a very minor effect on the aggregation rate. Mutation A227D resulted in a significant decrease of the aggregation rate (to 50%), which was even more pronounced when combined with T225E mutant (to 40%). Combining mutations from different aggregation-prone regions resulted in the strongest decrease of aggregation for mutants M153KT225E and M153KA227D (to 45%). Asterisks over the error bars indicating the p-value mean: "*" $p<0.05$, "" $p<0.01$, "*" $p<0.001$ and "****" $p<0.0001$. FIG. 6C: A plot showing number of aggregates per cell for YFP, SS7-YFP and selected improving mutations in transiently transfected HeLa cells. A decrease in number of aggregates per single cell in comparison to SS7-YFP could be observed for mutants Y151E, T225EA227D, M153KA227D and A154PA227D. FIG. 6D: A plot illustrating the total area of the aggregates per cell for YFP, SS7-YFP and selected improving mutations in transiently transfected HeLa cells. The smaller aggregate size was observed in the case of mutants Y151E, T225EA227D and M153KA227D. FIG. 6E: A plot showing number of aggregates per cell for YFP, SS7-YFP and selected improving mutations in transiently transfected U2OS cells. Mutations Y151E and T225EA227D resulted in reducing the number of aggregates per cell. FIG. 6F: A plot illustrating the total area of the aggregates per cell for YFP, SS7-YFP and selected improving mutations in transiently transfected U2OS cells. The smaller aggregate size was observed in the case of mutants T225EA227D, Y151E and M153KA227D.

FIG. 7A: A heat map version of the MASS plot (for Mutant Aggregation & Stability Spectrum) for more than 70,000 mutations generated during the SolubiS analysis for the 585 high-quality PDB structures. The X-axis shows the change in TANGO score, the Y-axis shows the change in FoldX structural stability associated with the mutation and the color code indicates the frequency of occurring mutations with that ΔTANGO and ΔΔG profile. The mutations that maximally reduce aggregation while preserving thermodynamic stability are indicated on the key within the box. FIG. 7B: A bar chart demonstrating the percentage of SolubiS mutations per structural class: (α) all α helical, (β) all β sheet, (α/β) mixed a helix and β sheet and (α+β) combined α helix and β sheet. The percentage of mutations identified using SolubiS is very similar for all SCOP classes. FIG. 7C: A bar chart showing the percentage of different domains within SCOP classes with at least five SolubiS mutations. All SCOP classes have a similar percentage of SolubiS mutants per class.

FIG. 8: Differential scanning calorimetric (DSC) data that show that the mutant PA (S588L/T605E) aggregates at higher temperature compared to the wild-type PA.

FIG. 9: Mouse macrophage cells are treated with wild-type PA and lethal factor and compared to the treatment of mutant PA (S588L/T605E) and lethal factor. It is shown that not only the biological activity is preserved for the mutant PA, but that the activity is also higher.

FIG. 10: Effect of the toxicity of wild-type PA and lethal factor compared to mutant PA (S588L/T605E) and lethal factor after heat stress treatment at 45° C. It is shown that the mutant PA has a significant preservation of the activity when subjected to heat stress.

DETAILED DESCRIPTION

The disclosure will be described with respect to particular embodiments and with reference to certain drawings but the disclosure is not limited thereto, but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated.

Furthermore, the terms "first," "second," "third," and the like, in the description and in the claims are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

The following terms or definitions are provided solely to aid in the understanding of the disclosure. Unless specifically defined herein, all terms used herein have the same meaning as they would to one skilled in the art of the present disclosure. Practitioners are particularly directed to Sambrook et al., *Molecular Cloning: A Laboratory Manual,* 2$^{nd}$ ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art. The definitions provided herein should not be construed to have a scope less than understood by a person of ordinary skill in the art.

In the present disclosure, the standard one-letter notation of amino acids will be used. Typically, the term "amino acid" will refer to "proteinogenic amino acid," i.e., those amino acids that are naturally present in proteins.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present disclosure, "sequence identity" will be understood to mean the "match percentage" calculated by the DNASIS® computer program (Version 2.5 for windows; available from Hitachi Software Engineering Co., Ltd., South San Francisco, Calif., USA) using standard defaults as used in the reference manual accompanying the software. "Similarity" refers to the percentage number of amino acids that are identical or constitute conservative substitutions. Similarity may be determined using sequence comparison programs such as GAP (Deveraux et al. 1984, *Nucleic Acids Research* 12, 387-395). In this way, sequences of a similar or substantially different length to those cited herein might be compared by insertion of gaps into the alignment, such gaps being determined, for example, by the comparison algorithm used by GAP.

The terms "aggregation-nucleating regions" or "aggregation-prone regions" or "beta-aggregation regions" or "self-association regions" are equivalent and refer to regions identified in proteins that are responsible for inducing the aggregation of the proteins. What follows the sequence constraints of these regions are further clarified. Mutational studies of the kinetics of aggregation of full-length proteins revealed simple correlations between aggregation and physico-chemical properties such as β-sheet propensity, hydrophobicity and charge. This stimulated the development of computer algorithms that can identify the aggregation-nucleating regions in the amino acid sequence of a protein. One of these is the Zyggregator algorithm of Dobson et al. (Pawar et al., *J. Mol. Biol.* 350:379-392 (2005)), which identifies aggregation-prone sequences by comparing the aggregation-propensity score of a given amino acid sequence with an average propensity calculated for a set of sequences of similar length. The statistical mechanics algorithm TANGO (Fernandez-Escamilla et al., *Nat. Biotechnol.* 22:1302-1306 (2004)), on the other hand, balances the physico-chemical parameters mentioned above, supplemented by the assumption that an amino acid is fully buried in the aggregated state: this means it becomes fully desolvated and entropically restricted. From an input sequence, TANGO generates an extensive sample of fragments for which competing structural propensities, such as helix or hairpin formation, are considered. All the fragments are then balanced in a global partition sum, which allows the identification of sequence regions that predominantly form aggregates. The TANGO algorithm has an accuracy of more than 90% for a set of 176 experimentally validated peptides (Fernandez-Escamilla et al., *Nat. Biotechnol.* 22:1302-1306 (2004)). Importantly, both the Zyggregator algorithm and TANGO perform well for peptides and denatured proteins. For globular proteins, a partly folded molecule can either refold to the native state or misfold into an aggregated state. As a result, both reactions are in competition and a precise understanding of the kinetics is essential to predict the final outcome in terms of folding or misfolding/aggregation. Hence, in the context of this disclosure, it is important to identify sequences in globular proteins that kinetically favor the reduction of aggregation. The Tango algorithm has been described in more detail elsewhere. (See, particularly, Fernandez-Escamilla et al., *Nat. Biotechnol.* 22:1302-1306, 2004, especially the Methods section on pages 1305 and 1306, herein specifically incorporated by reference. See also the Supplementary Notes 1 and 2 of the same article for further details on the methods and the data sets used for the calibration and the testing of the TANGO algorithm.) Briefly, to predict aggregation-nucleating regions of a protein (or polypeptide), TANGO simply calculates the partition function of the phase-space. To estimate the aggregation tendency of a particular amino acid sequence, the following assumptions are made: (i) in an ordered beta-sheet aggregate, the main secondary structure is the beta-strand; (ii) the regions involved in the aggregation process are fully buried, thus paying full solvation costs and gains, full entropy and optimizing their H-bond potential (that is, the number of H-bonds made in the aggregate is related to the number of donor groups that are compensated by acceptors; an excess of donors or acceptors remains unsatisfied); (iii) complementary charges in the selected window establish favorable electrostatic interactions, and overall net charge of the peptide inside but also outside the window disfavors aggregation. TANGO can be accessed on the World Wide Web.

Figure 1A:
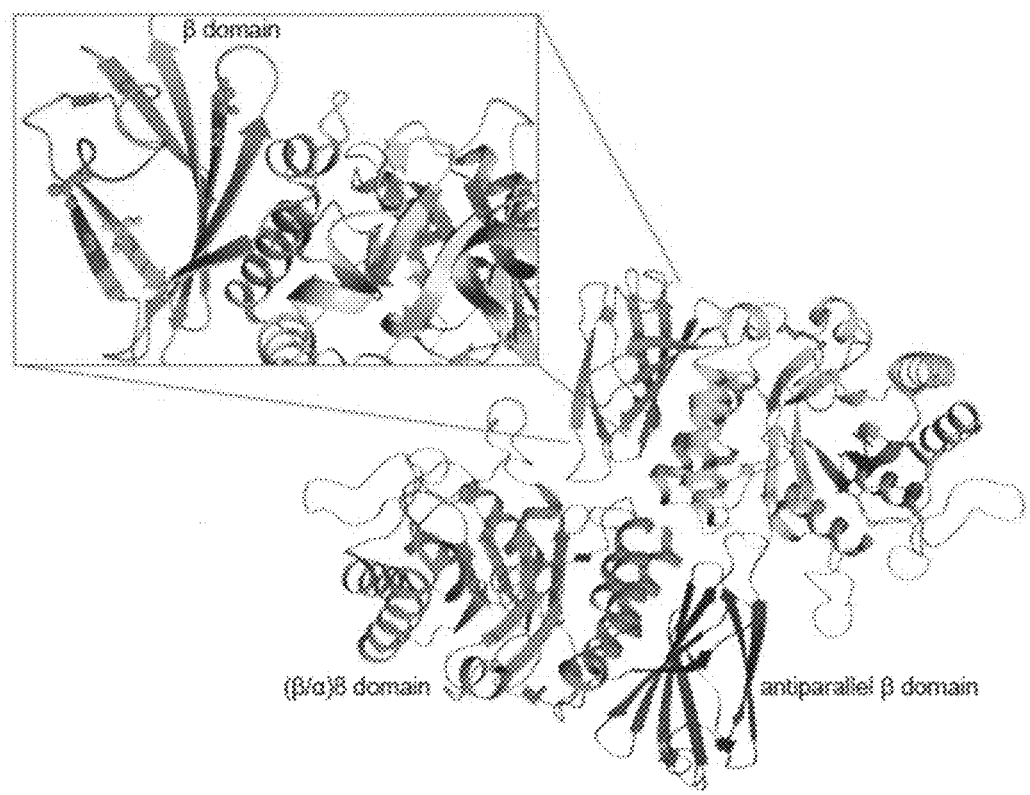
FIGS. 1A-1D: Structure and aggregation propensity of human wild-type α-Galactosidase.

A high Tango score of a sequence stretch typically corresponds to a sequence with high (and kinetically favorable) beta-aggregation propensity. In the present disclosure, the sequence space of "the lowest tango-scoring sequences" of a particular variant of a protein generated in the context of this disclosure are preferred.

It can be calculated that more than 80% of all proteins have at least one aggregation-nucleating segment within their primary sequence. As a result, protein aggregation is often encountered when proteins are overexpressed or recombinantly produced. Moreover, aggregation represents a major liability with respect to the immunogenicity of biotherapeutics. However, redesigning globular proteins to eliminate aggregation is not a straightforward task as most aggregation-nucleating sequences are part of the hydrophobic core and, therefore, difficult to mutate without disrupting protein structure and function. In this disclosure, a minimal redesign method was developed, termed "SolubiS," to abrogate aggregation by silencing aggregation-nucleating sequences through the introduction of specific mutations, which are selected to maximally reduce the intrinsic aggregation propensity of the sequence while preserving thermodynamic stability of the functional protein. The present method allows sifting hundreds to thousands of mutations, simultaneously evaluating protein aggregation and stability, typically producing 1 to 5 appropriate mutations per target protein. In the appended examples, the method is exemplified for three relevant proteins: i) human α-Galactosidase, which is currently used in enzyme replacement therapy for Fabry disease, ii) Yellow Fluorescent Protein (YFP), an important research biologic, and iii) Anthrax Protective Antigen (PA), which is a key toxin secreted by *Bacillus anthracia*. In each case, mutants were identified that displayed a marked reduction in protein aggregation upon overexpression while preserving both stability and functionality. Furtheiniore, an in silico analysis of a non-redundant set of 443 high-resolution crystallographic structures shows that 75% of globular proteins with a high aggregation propensity are amenable to the redesign strategy, showing that the invented method is broadly applicable for the improvement of globular proteins.

Accordingly, the disclosure provides in a first embodiment, a method for the production of a reduced aggregating variant of a protein that has at least two aggregation-nucleating regions, the method comprising the following steps: a) determining the aggregation-nucleating region in the protein, b) generating a list of variant proteins wherein each variant protein has a changed amino acid to either R, K, E, D or P on at least one amino acid position in the determined aggregation-nucleating regions, c) calculating for each of the variants the predicted aggregation score and the predicted change in thermodynamic stability with respect to the wild-type protein, and d) producing a reduced aggregating variant, which is derived from the list, wherein the variant has at the same time a maximally reduced aggregation score, a maximal preservation of thermodynamic stability and no structural changes with respect to the wild-type protein.

The term "reduced aggregating variant of a protein" refers to a variant protein (or a mutant protein) that has, with respect to the wild-type protein (i.e., the naturally occurring protein), a 10%, a 20%, a 30%, a 40%, a 50%, a 60%, a 70%, an 80%, a 90% or even higher percentage of reduced aggregation. Non-limiting methods for measuring a reduced aggregation are herein further provided in the appended examples. The term "aggregating nucleating regions" is herein described before and non-limiting examples of methods are described how to identify (or to determine which is an equivalent word) "aggregating nucleating regions" in a protein. In a particular embodiment, the protein from which it is started to develop a reduced aggregating variant has at least two, at least three, at least four or more aggregating nucleating regions. The aggregating nucleating regions that are identified are in silico modified, wherein at least one of the amino acid positions present in the aggregating nucleating region are changed toward either an R, a K, an E, a D or a P. Thus, a list of variant proteins is generated wherein each amino acid position of the aggregating nucleating regions is changed in five different amino acids (i.e., an R, a K, an E, a D or a P). Thus, for each specific amino acid position present in the aggregating nucleating region, five different variants are generated. In another particular embodiment, at least two of the amino acid positions present in the aggregating nucleating region are changed toward either an R, a K, an E, a D or a P. In another particular embodiment, at least two of the amino acid positions can be changed toward an R, a K, an E, a D or a P and the at least two amino acid positions are modified in two different aggregating nucleating regions of the protein.

In a particular embodiment, a reduced aggregating variant of a protein comprises at least one mutation in one of its aggregation-nucleating regions. In another particular embodiment, a reduced aggregating variant of a protein comprises at least two mutations in in one of its aggregation-nucleating regions. In yet another particular embodiment, a reduced aggregating variant of a protein comprises at least two mutations, each mutation in a different aggregation-nucleating region.

For each variant protein generated, the predicted aggregation score is calculated by use of algorithms described hereinbefore. In addition, for each variant protein generated, the predicted thermodynamic stability is calculated using methods described herein (e.g., the FoldX algorithm). Other algorithms to calculate the thermodynamic stability are known to the person skilled in the art. A non-limiting example to determine the thermodynamic stability is the molecular modeling software Rosetta (R. Das and D. Baker (2008) *Annual Rev. Biochemistry* 28:363-382).

The present method hinges on the availability of the three-dimensional structure of the protein one aims to modify into a reduced aggregating variant protein. Therefore, in the method of the disclosure, the most optimal reduced aggregating variant protein that is produced is derived from the generated list of all the variants, and needs to have, at the same time, a maximally reduced aggregation score, a maximal preservation of the thermodynamic stability and, in addition, has no structural predicted changes with respect to the wild-type protein. The following examples show that only a very limited amount of variant proteins are produced that fulfill the above conditions. In a particular embodiment, 1, 2, 3, 4, 5, 6, 7, 8, 9 or 10 variant proteins are produced with the methods of the disclosure. In another particular embodiment, less aggregating variants of a protein that are produced by introducing a mutation in one aggregation-nucleating region can be combined with variants that are produced by introducing a mutation in another aggregation-nucleating region, i.e., by combining two identified separate mutant variants into one new variant. Specific examples are provided in the appended examples.

In yet another embodiment, the disclosure provides a method for the production of a reduced aggregating variant of a protein that has at least two aggregation-nucleating regions, the method comprising the following steps: a) determining the aggregation-nucleating region in the protein, b) generating a list of variant proteins wherein each variant protein has a changed amino acid to either R, K, E, D or P on at least one amino acid position in the determined aggregation-nucleating regions, c) calculating the predicted aggregation score and the predicted change in thermodynamic stability with respect to the wild-type protein for each of the variants, d) introducing at least one compensatory mutation outside at least one of the aggregation-nucleating regions with the purpose of preserving the thermodynamic stability of the protein and e) producing a reduced aggregating variant, wherein at least one mutation is derived from the list and wherein, additionally, also at least one compensatory mutation is present in the variant, wherein the variant has, at the same time, a maximally reduced aggregation score, a maximal preservation of thermodynamic stability and no structural changes with respect to the wild-type protein.

The term "compensatory mutation" refers to an amino acid change in the protein that is introduced into either R, K, E, D or P, in addition to at least one change of one of the amino acids of the aggregation-nucleating region. Often, this change in the aggregation-nucleating region of the protein reduces the thermodynamic stability of the resulting variant protein and a compensatory mutation needs to be introduced to compensate for the reduction of thermodynamic stability. Typically, a compensatory mutation is situated outside the aggregation-nucleating region that comprises a mutation.

In yet another embodiment, the disclosure provides a reduced aggregation variant of a protein that has at least two aggregation-nucleating regions that is obtainable by a) determining at least two aggregation-nucleating region in the protein, b) generating a list of variant proteins, wherein each variant protein has a changed amino acid to either R, K, E, D or P on at least one amino acid position in the determined aggregation-nucleating regions, c) calculating the predicted aggregation score and the predicted change in thermodynamic stability with respect to the wild-type protein for each of the variants, and d) producing a reduced aggregating variant, which is derived from the list, wherein the variant has at the same time a maximally reduced aggregation score, a maximal preservation of thermodynamic stability and no structural changes with respect to the wild-type protein.

In yet another embodiment, the disclosure provides a reduced aggregation variant of a protein that has at least two aggregation-nucleating regions that is obtainable by a) determining at least two aggregation-nucleating region in the protein, b) generating a list of variant proteins wherein each variant protein has a changed amino acid to either R, K, E, D or P on at least one amino acid position in the determined aggregation-nucleating regions, c) calculating the predicted aggregation score and the predicted change in thermodynamic stability with respect to the wild-type protein for each of the variants, and d) introducing a compensatory mutation outside at least one of the aggregation-nucleating regions with the purpose of preserving the thermodynamic stability of the protein and e) producing a reduced aggregating variant, which is derived from the list, wherein the variant has at the same time a maximally reduced aggregation score, a maximal preservation of thermodynamic stability and no structural changes with respect to the wild-type protein.

The present method offers a variety of possible applications. One application is, for example, in the field of enzyme replacement therapy. Several proteins can be optimized into reduced aggregating variants. Non-limiting examples of such proteins are, for example, glucocerebrosidase, alfa-galactosidase A, alpha-galactosidase, alpha-L-iduronidase and GlcNAc phosphotransferase. Yet another application is the generation of so-called "biobetters" that are improved (i.e., reduced aggregating variants of existing biological). Non-limiting examples are known in the art as "biobetters," which can be produced from interferon-beta, insulin, granulocyte macrophage-stimulating factors and members of the interleukin family. Yet another application is in the field of affinity chromatography. For example, reduced aggregation-binding proteins can be designed that have a reduced aggregation in apolar solvents. Yet another application is in the field of agrobiotechnology. It can be envisaged that certain crucial proteins suffer from aggregation when crops encounter conditions of abiotic stress such as heat, cold or salt. By generating variants of such crucial proteins that are less prone to aggregation, novel transgenic crops can be generated that are resistant to abiotic stress. Yet another application is in the field of enzymology. Novel enzyme variants can be produced with the current method that are less prone to aggregation and hence remain active for a longer period than the corresponding wild-type enzyme. Yet another application is in the field of protein production. Less aggregation-prone variants will show an increased expression level and makes the downstream purification processing easier.

In addition, this disclosure also provides specific examples. In one specific example, reduced aggregation variants of alpha-galactosidase A are generated. The amino acid sequence of alpha-galactosidase A is depicted in SEQ ID NO:1 (Alpha-Gal A (genbank identifier NP_000169)).

Thus, in a specific embodiment, a reduced aggregation variant of the alpha-galactosidase A protein (wild-type is depicted in SEQ ID NO:1) is provided, which is selected from the list consisting of i) A348R/A368R, ii) A348R/A368P, iii) A348R/A368R/S405L and iv) A348R/A368P/S405L.

Accordingly, in a specific embodiment, the disclosure provides a reduced aggregation variant of the alpha-galactosidase A protein (wild-type is depicted in SEQ ID NO:1), which is selected from the list consisting of i) A348R/A368R, ii) A348R/A368P, iii) A348R/A368R/S405L and iv) A348R/A368P/S405L for the treatment of Fabry disease.

In yet another specific example, reduced aggregation variants of yellow fluorescent protein, citrine variant, are generated. The amino acid sequence of yellow fluorescent protein, citrine variant is depicted in SEQ ID NO:2 (Yellow Fluorescent Protein (YFP) citrine variant).

In another specific embodiment, a reduced aggregation variant of the yellow fluorescent protein (wild-type sequence is depicted in SEQ ID NO:2) selected from the list consisting of i) M153K/T225E, ii) M153K/A227D, iii) Y151E, iv) M153K/A227D and v) T225E/A227D.

In yet another specific example, a reduced aggregation variant of *Bacillus anthracis* Protective Antigen is provided. The amino acid sequence of the *Bacillus anthracis* Protective Antigen is depicted in SEQ ID NO:3.

In another specific embodiment, a reduced aggregation variant of the *Bacillus anthracis* Protective Antigen (wild-type sequence is depicted in SEQ ID NO:3) is S588L/T605E.

It is to be understood that although particular embodiments, specific configurations as well as materials and/or molecules, have been discussed herein for cells and methods according to this disclosure, various changes or modifications in form and detail may be made without departing from the scope and spirit of this disclosure. The following examples are provided to better illustrate particular embodiments, and they should not be considered limiting the application. The application is limited only by the claims.

EXAMPLES

1. The SolubiS Method

Protein aggregation-nucleating regions can be identified using specialized software, which have been reviewed elsewhere (Belli, Ramazzotti et al. 2011). In the present disclosure, the statistical thermodynamics algorithm TANGO (Fernandez-Escamilla, Rousseau et al. 2004) was employed to detect aggregation-nucleating regions in the target sequence. Proteins were selected for which high-resolution crystallographic structures are available so that the topological position of the aggregating regions can be visualized using atomic structure viewers. The structural information also enables the use of an atomic force field to eliminate mutations that thermodynamically destabilize the native structure. Again, methods for predicting the mutational effects on protein stability have been reviewed elsewhere (Chen and Shen 2009) and the results shown here were obtained with the FoldX forcefield (Schymkowitz, Borg et al. 2005). Two classes of mutations can be designed to reduce protein aggregation: (i) Mutations that eliminate or strongly reduce the intrinsic aggregation propensity of the sequence, thereby slowing down the aggregation reaction and (ii) Mutations that stabilize the interaction of the aggregating region with the rest of the structural domain in which it resides, thus providing additional protection from solvent exposure. In the ideal case, mutations can be identified that unify both goals, but often a combination of mutations is required to maximally suppress aggregation. Reduction of intrinsic aggregation is usually achieved by the introduction of aggregation-breaking residues, called gatekeepers (Rousseau, Serrano et al. 2006; Monsellier and Chiti 2007), in the aggregation-nucleating sequences. Since the gatekeepers consist of the charged amino acids (Arg, Lys, Glu, Asp) and proline, most often they need to be placed in exposed regions in order not to disturb the hydrophobic core of the protein. The SolubiS method thus consists in systematically mutating the residues residing within a mostly structurally buried aggregation-prone region (or TANGO zone) to each of the gatekeeper residues and calculating the consequent change in TANGO score, as well as the change in the thermodynamic stability of the protein using FoldX (this process will be called gatekeeper scan in what follows). In the case where the gatekeeper residues can only be placed by compromising the thermodynamic stability of the protein, we scan for compensatory mutations using the FoldX algorithm. During the whole process, mutation of residues were avoided that are known to be involved in catalysis or binding.

2. Generation of Less Aggregating Variants of Alpha-Galactosidase A (Alpha-Gal)

Figure 1B:
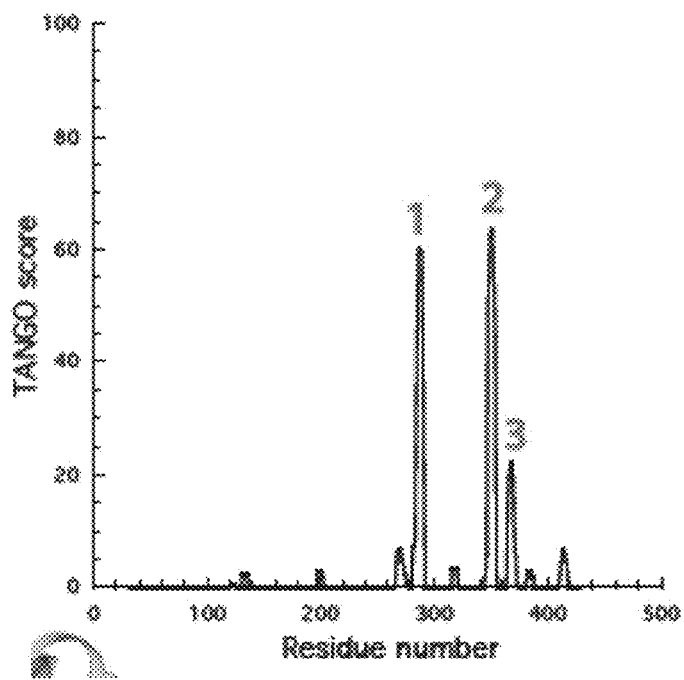

Human α-Gal is a lysosomal hydrolase that cleaves neutral glycosphingolipids with terminal α-linked galactosyl moieties, mainly globotriaosylceramides (Gb3). Deficiency in the activity of this glycoprotein results in accumulation of the enzyme's substrates, leading to Fabry disease (FD) (OMIM 301500), a metabolic X-linked inherited lysosomal storage disorder (LSD) (Brady, Gal et al. 1967; Eng and Desnick 1994). The structure is a homodimer in which each monomer contains a (βα) domain (FIG. 1A, central part, yellow and green parts) where the active site is found, and an antiparallel β domain (FIG. 1A, orange and blue). The regions predicted by TANGO (FIG. 1B) to be highly aggregation prone (indicated with 1, 2 and 3 and colored in red in FIG. 1A, upper left) cluster in the β-domain and the interface between the domains. In particular, region 3 is likely to be at risk of nucleating aggregation from visual inspection of the structure given its edge position in the beta-sheet. The results of computational gatekeeper scan of each of the aggregation-prone regions of α-Gal is shown as a MASS-plot (Mutant Aggregation & Stability Spectrum), i.e., a scatter plot (FIG. 1C) of the change in thermodynamic stability ($\Delta\Delta G$ values calculated by FoldX in kcal/mol) versus change in the intrinsic aggregation propensity (values calculated by TANGO, range between 0 and 100 per amino acid residue) associated to each aggregation-nucleating region. These plots allow for easy identification of ideal mutations, with large negative values on both axes, i.e., mutations that reduce the intrinsic aggregation propensity while increasing the thermodynamic stability of an aggregation-nucleating region. For TANGO region 1, no such mutations could be identified, owing mainly to the fact that this region is completely buried inside the tightly packed domain interface. TANGO regions 2 and 3 display one such mutation each (A348R and A368P), as well as the possibility for stabilizing region 3 with little predicted effect of intrinsic aggregation (A368R) (FIG. 1C).

Figures 1C, 1D:
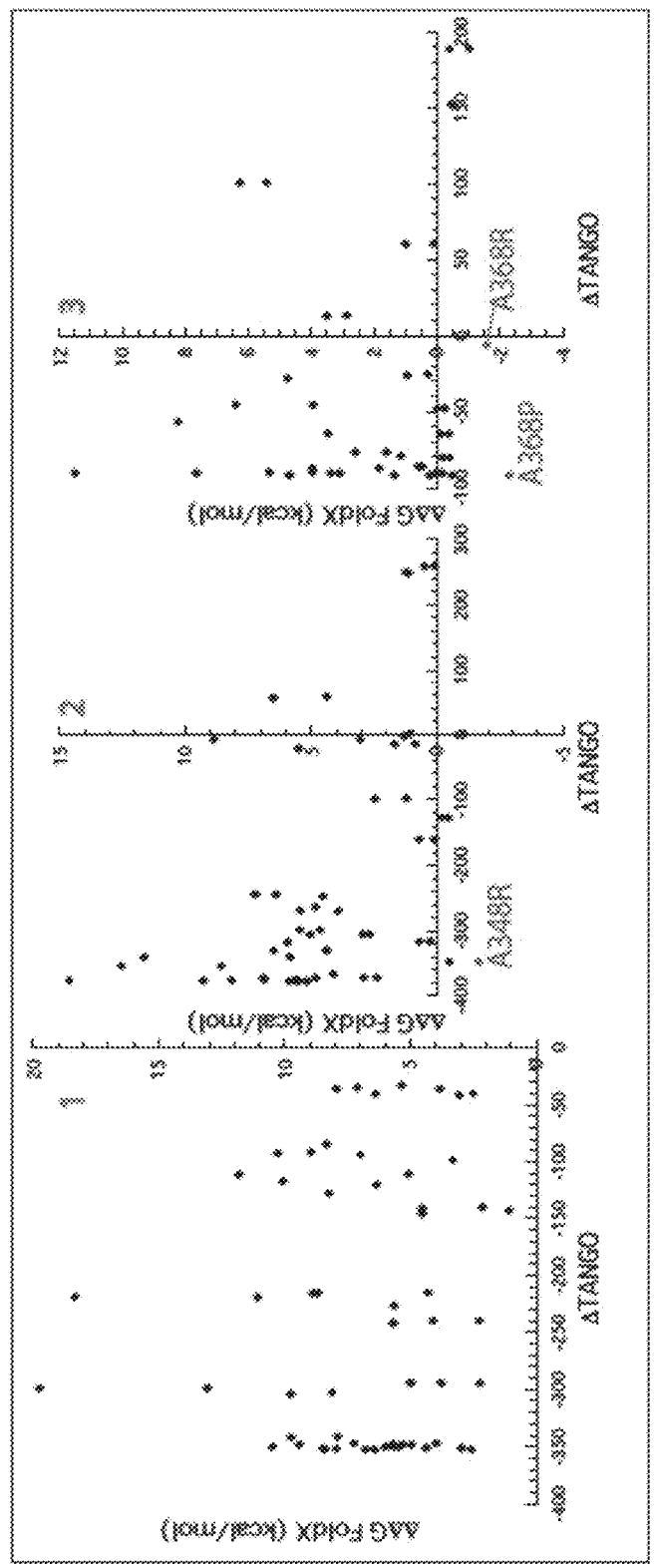
Figure 2A:
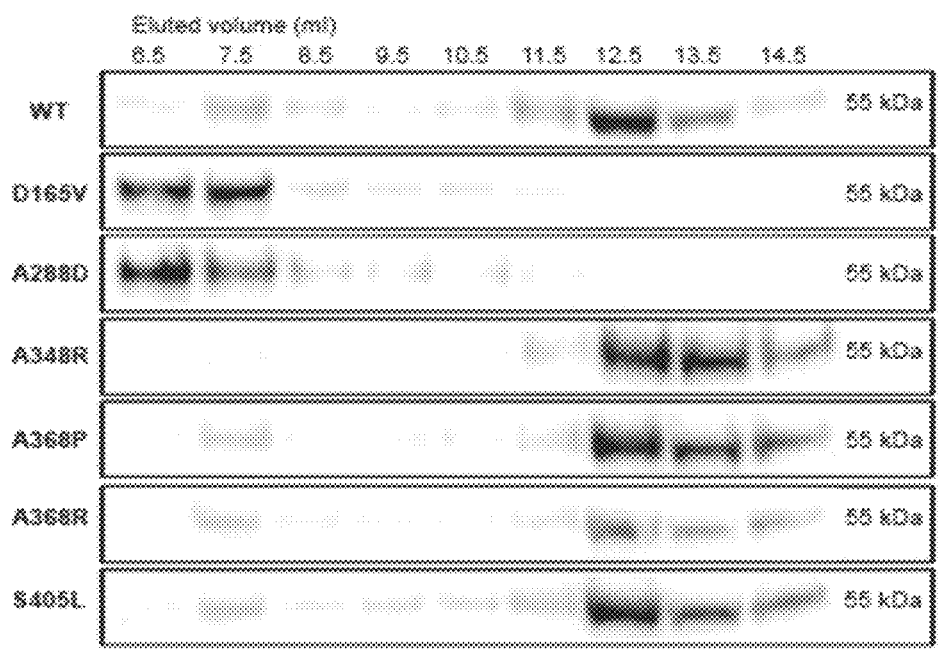
FIGS. 2A-2D: Effect of the single improving mutation on α-Gal aggregation and activity.
Figure 2B:
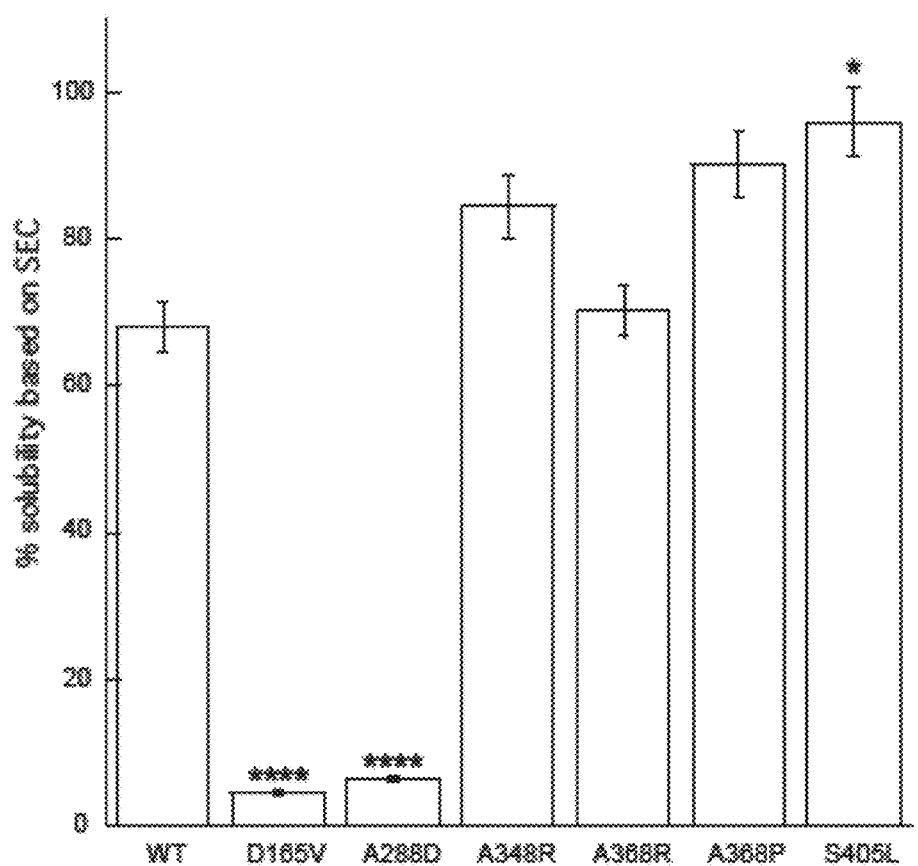
Figure 2C:
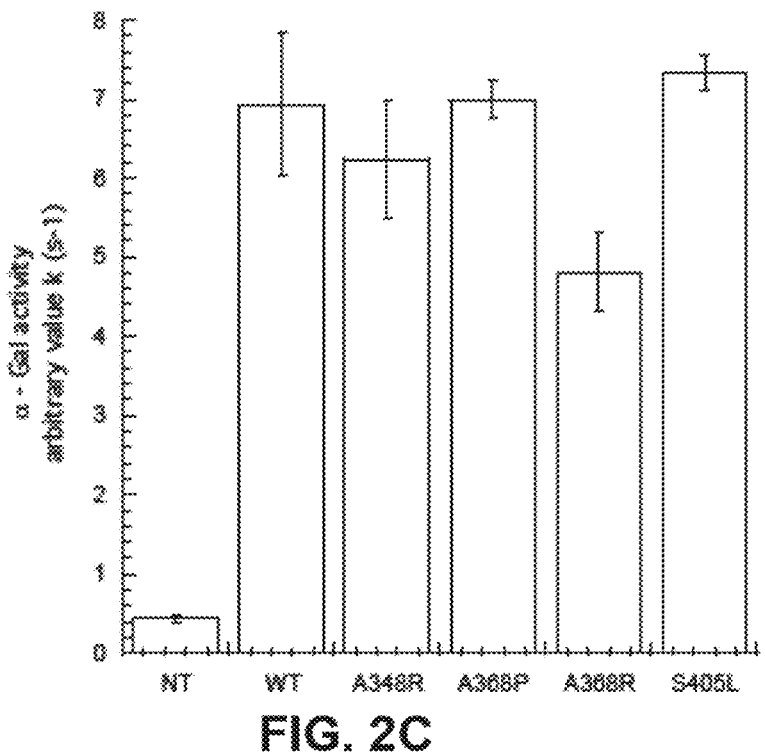
Figure 2D:
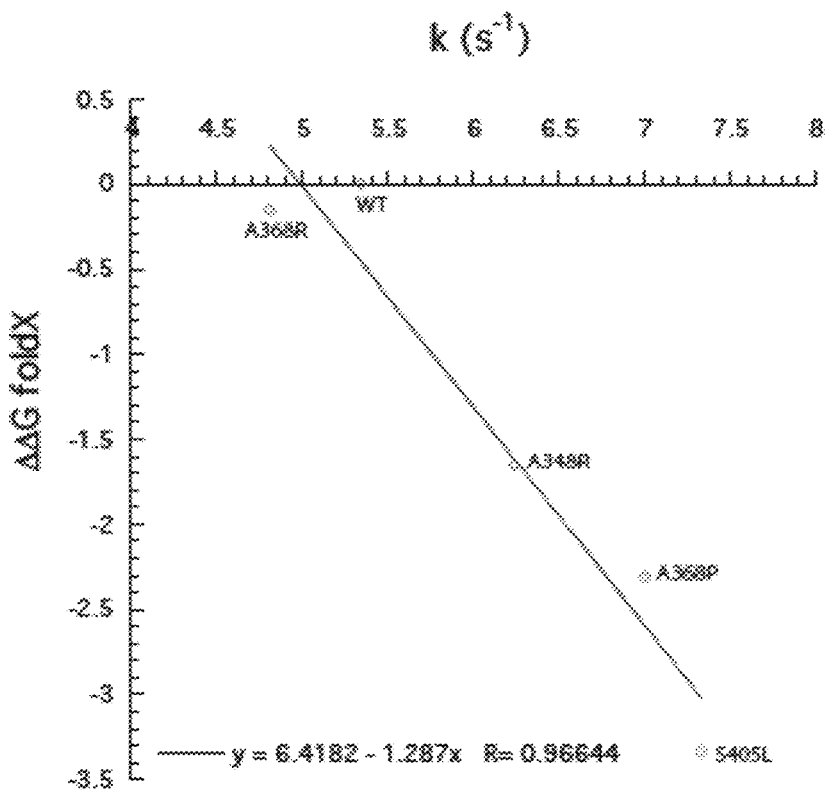

In addition, an exhaustive mutation scan was performed throughout the β domain and the mutations were listed with a predicted beneficial effect on thermodynamic stability of greater than 2 kcal/mol in the table set in FIG. 1D. The single most stabilizing mutation (S405L, $\Delta\Delta G_{FoldX}=-3.34$ kcal/mol) tightens the interaction of the edge beta strand (the site of TANGO region 3) with the rest of the domain. Based on this rationale, the effect of these mutations was investigated in an experimental setup. For this purpose, the full-length cDNA sequence encoding human α-Gal was cloned into the pcDNA4/TO/myc-His vector and the individual mutations were generated using site-directed mutagenesis. For comparison, D165V and A288D mutants were generated, which are associated with Fabry disease and were previously found to be particularly aggregation-prone. The entire set of mutant and wild-type proteins in HeLa cells were transiently overexpressed and the solubility of α-Gal in the lysates was observed using size-exclusion chromatography on a S200 column, followed by Western blot (see material and methods section for experimental details). As is shown in FIG. 2A, the wild-type protein elutes mainly as a dimer but also shows faint bands in the SEC fractions that elute to volumes corresponding to large molecular sizes (exclusion limit of this column is 600 kDa), consistent with partial misfolding and aggregation of wild-type α-Gal. As expected, the disease-associated mutations D165V and A288D show a significant increase of these high molecular weight assemblies. The individual mutations selected by SolubiS to reduce aggregation show a modest decrease in the high-molecular fractions when compared to wild-type α-Gal that is most pronounced for A348R mutant (FIG. 2A). Quantification of the solubility revealed that aggregating mutants (D165V and A288D) were highly insoluble (<10%), whereas single improving mutants reached around 80% to 90% of total solubility in comparison to 65% for wild-type (FIG. 2B). The enzymatic activity α-Gal was determined by following the conversion of the fluorogenic substrate 4-methylumbelliferyl-α-D-galactopyranoside (4-MU-α-Gal) over time. Consistently, single improving mutants showed similar activity in comparison to wild-type (only slightly reduced in the case of A368R mutant) (FIG. 2C), suggesting that the selected mutations do not affect the active site of the enzyme and, therefore, do not interfere with its enzymatic function. Interestingly, plotting experimental values of enzyme activity versus predicted change in thermodynamic stability showed very good correlation (FIG. 2D), showing that the predicted increased stability of the protein actually correlates to improved activity.

Overall, the effects of single SolubiS mutants show a decrease of misfolding and aggregation, an improved solubility, while leaving enzymatic activity unharmed. The fact that the observed improvements are overall modest is explained by the fact that α-Gal possesses three aggregation-nucleating regions; improving one region by a single mutation leaves it susceptible to aggregation by the other regions. It is, therefore, expected that targeting several zones in parallel by multiple mutants should have a synergistic effect on the solubility and enzymatic activity of α-Gal.

Figure 3A:
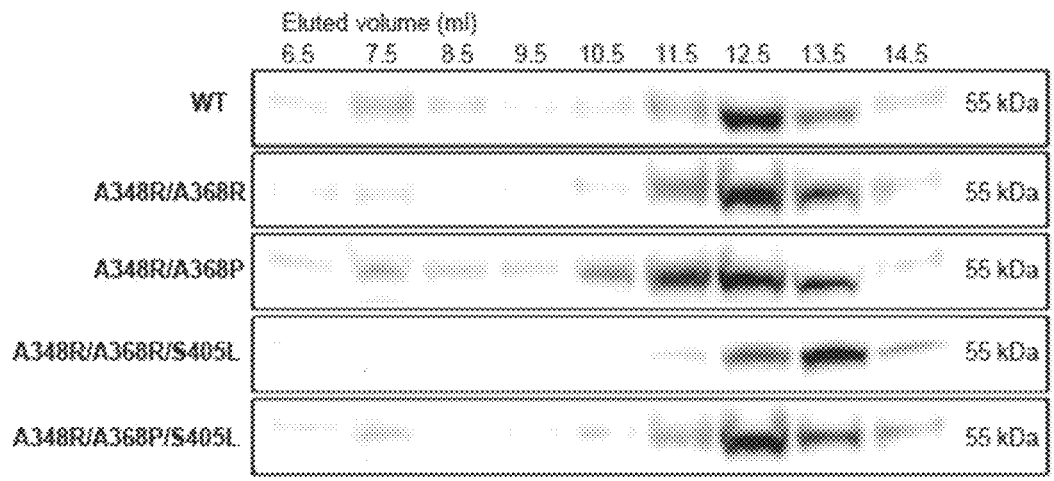
FIGS. 3A-3D: Effect of the double and triple improving mutation on α-Gal aggregation and activity.
Figure 3B:
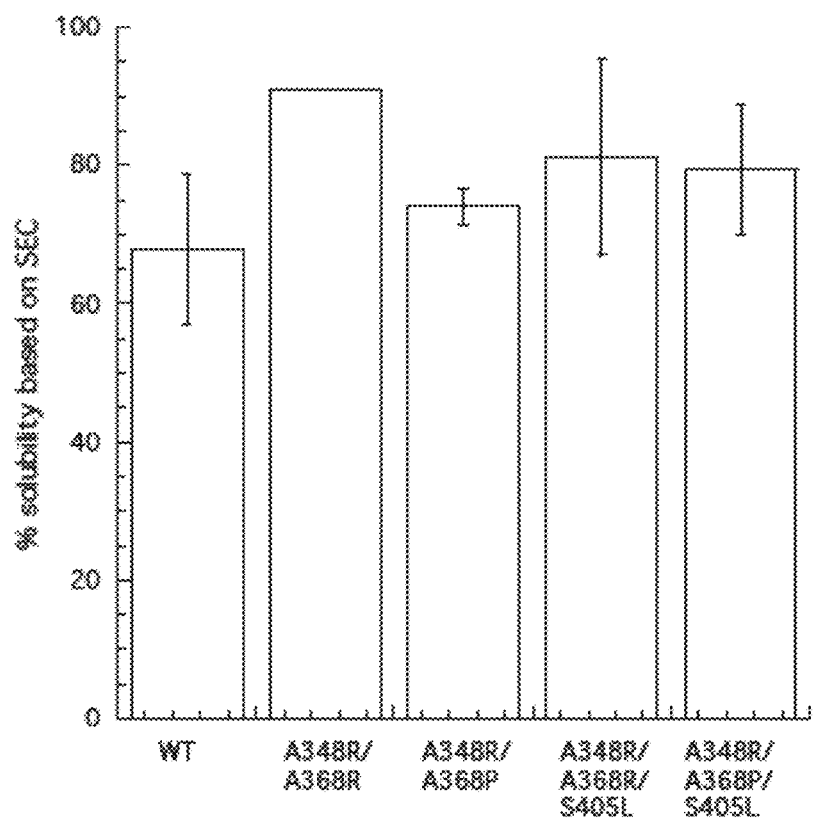
Figure 3C:
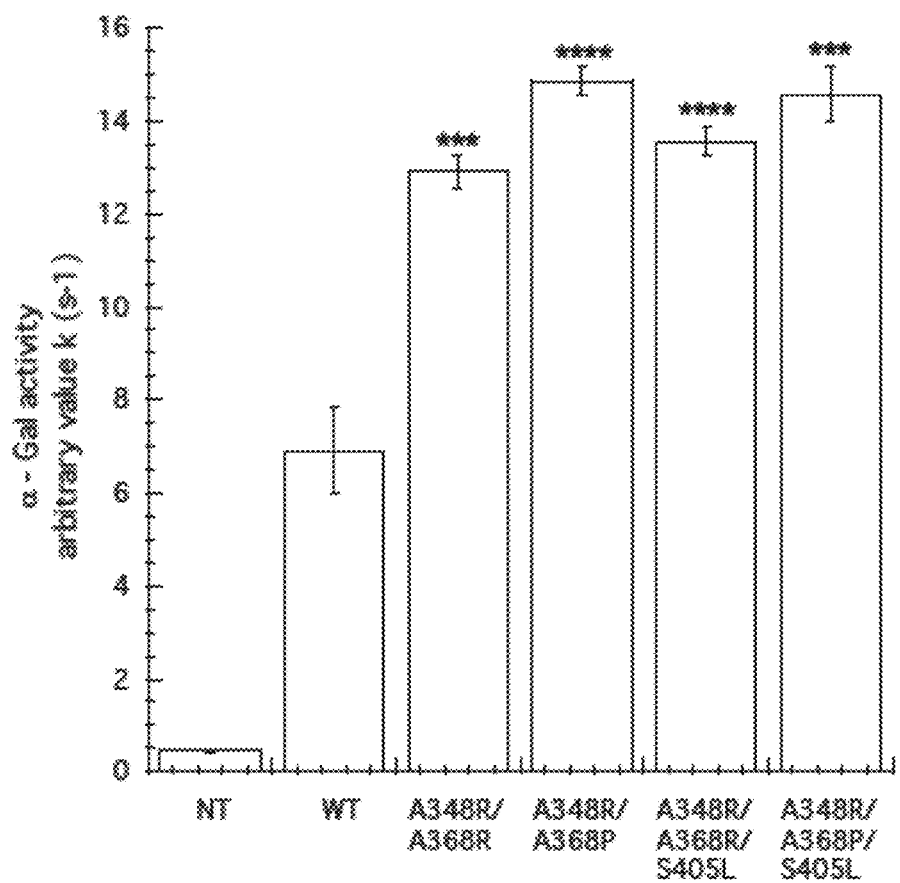
Figure 3D:
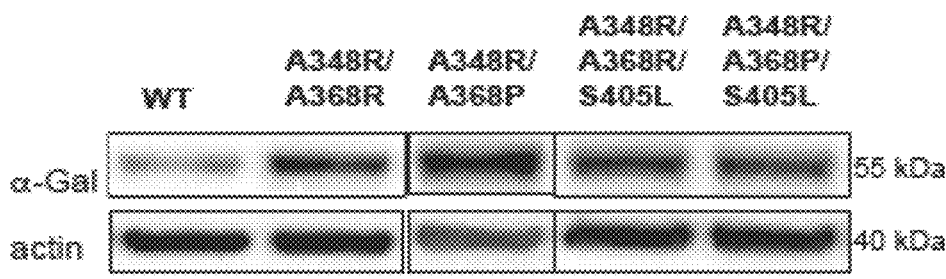

In order to determine the best combinations of mutations, several double (A348R/A368P and A348R/A368R) and triple mutants (A348R/A368P/S405L and A348R/A368R/S405L) were generated consisting of the single mutations in TANGO region 2 and TANGO region 3, as well as the stabilizing mutant S405L. Interestingly, a significant increase in the enzymatic activity was observed for all mutants compared to wild-type or the single mutants (FIG. 3C). Such an increase in activity could be caused by an increase in intrinsic activity or by more efficient protein folding, resulting in higher expression of native α-Gal. When investigated by western blot, it appeared that when equal amounts of plasmid DNA were transfected, this resulted in increased expression levels between the constructs (FIG. 3D) consistent with an increase in the protein folding efficiency and a more stable (less degradable) protein configuration, leading into more enzymatic activity. This is further confirmed by SEC fractionation: the double and triple mutants result in a higher yield of low molecular weight α-Gal. This is particularly striking for mutant A348R/A368R/S405L for which higher molecular forms are almost undetectable. Together, these data show that the rational redesign of α-Gal by SolubiS is able to generate double and triple mutants optimizing enzymatic activity by displaying improved foldability and expression.

3. Generation of Less Aggregating Variants of Yellow Fluorescent Protein (YFP)

Figure 4A:
FIGS. 4A-4C: Structure and aggregation propensity of yellow fluorescent protein.
Figure 4B:
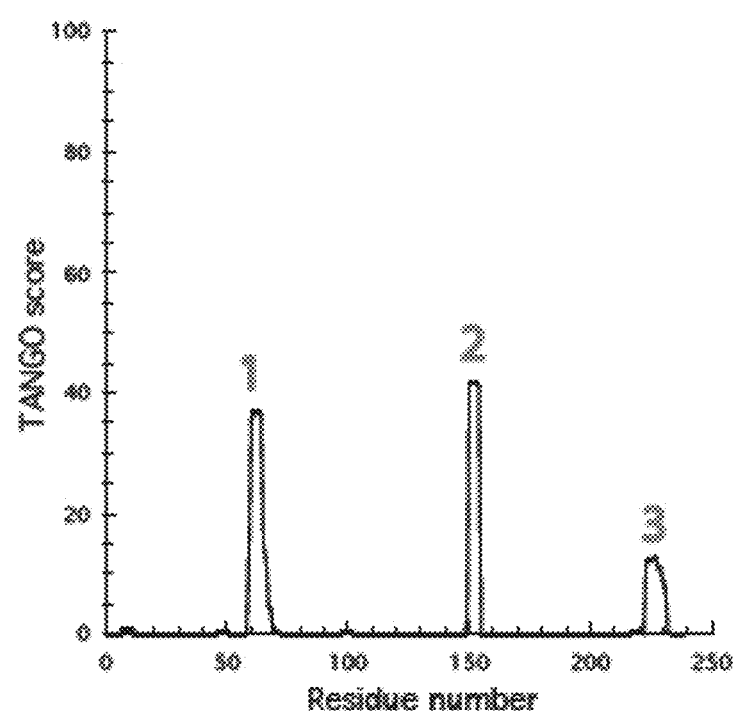
Figure 4C:
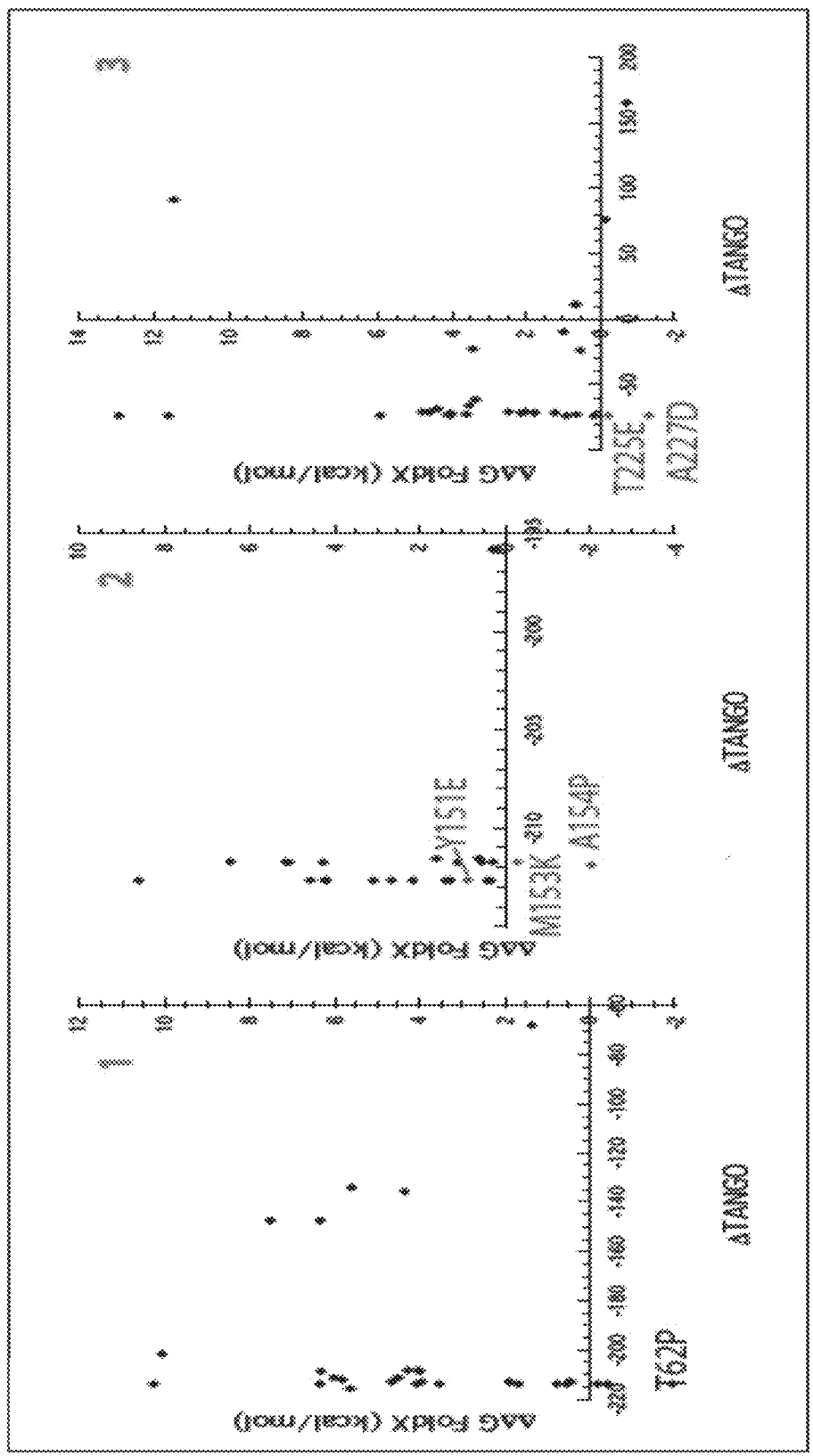
Figure 6A:
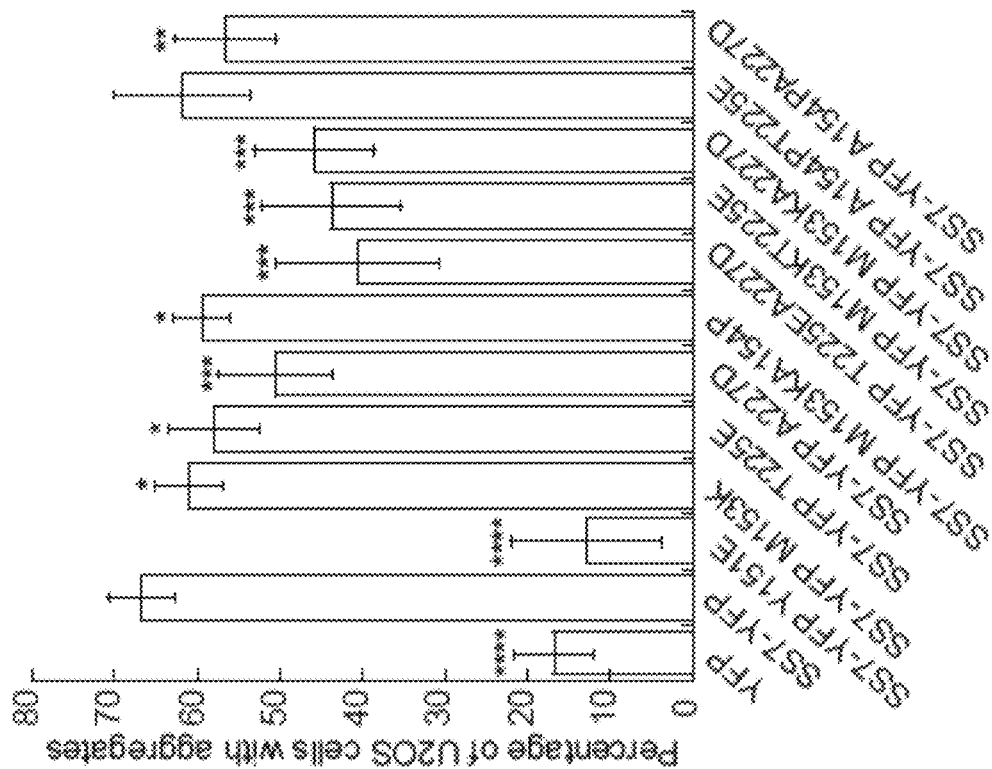
FIGS. 6A-6F: Aggregation levels and single cell data of SS7-YFP model fusion protein and its improving mutations in HeLa and U2OS cells.
Figure 6B:
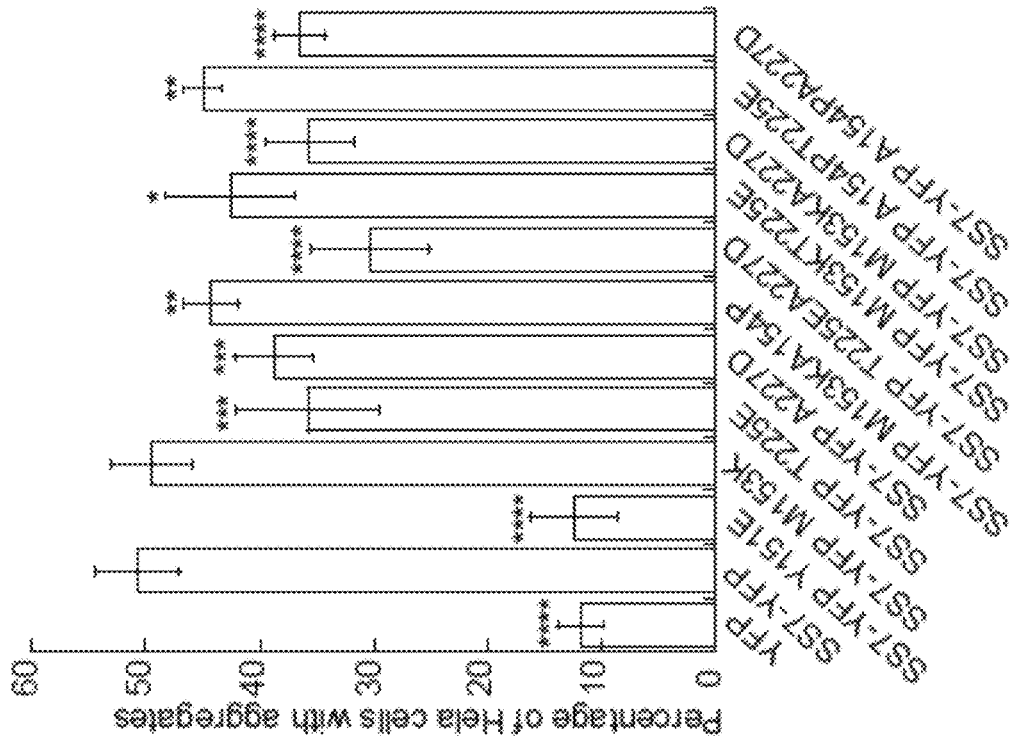

Fusion proteins often display loss of proper folding after fusion to certain targets resulting in mislocalization or functional inactivation. In order to investigate if this protein improvement method could reduce this problem, Aequorea Yellow Fluorescent Protein (YFP) citrine, a bright intrinsically fluorescent protein with a known high-resolution atomic structure, was selected (Griesbeck, Baird et al. 2001). The protein folds into the typical beta-barrel structure with a chromophore running through the center, which is formed by the cyclization of the backbone of residues 65-67 to form an imidazolidone structure (FIG. 4A). Analysis with TANGO reveals three aggregation-prone regions, indicated in red in the structure (FIG. 4B), and gatekeeper scans with FoldX and TANGO of the three regions (FIG. 4C), which revealed possible improving mutations in each TANGO region. As one of the TANGO regions corresponds to the chromophore center and it is known that mutation near this region alters the spectral properties of the fluorescent protein, mutations were avoided in this site and focused on optimizing the two remaining regions. Given the fact that the chromophore region is fully buried inside the beta barrel, lends further support to this strategy. Hence, Y151E, M153K and A154D were generated in TANGO region 2 and T225E and A227D were generated in TANGO region 3. Though the latter region has a relatively low TANGO score, it has a C-terminal rendering it susceptible to breathing motions, thereby probably facilitating aggregation. In order to mimic YFP misfolding by fusion, an N-terminal fusion was constructed of an aggregating peptide (LLRLTGW; SEQ ID NO:5) to citrine (FIG. 5, Panel A); in effect, this models the effect of a strongly aggregating protein fully exposing an aggregation-nucleating region. Quenching of fluorescence by aggregation has previously been used to screen for soluble Alzheimer's b-peptide variants. Here, the aggregating peptide was kept as a constant handicap and aim at increasing the capacity of YFP to cope with this additional burden. Normally, YFP expressed in mammalian cells distributes equally throughout the whole cell, however, combined with the aggregating peptide, it forms bright aggregates located in the cytoplasm (FIG. 5, Panel B), validating the fusion model. Using the model for aggregating fusion proteins (named SS7-YFP), it was decided to investigate the effect of selected improving mutations on the aggregation rate of YFP. For this purpose, single and double mutants in YFP were generated using site-directed mutagenesis and transiently overexpressed them in HeLa and U2OS cell lines. In order to obtain the most complete and detailed information about the aggregation pattern of SS7-YFP and its mutants (not only the number of cells with aggregates but also the number of aggregates per cell and the area of the aggregates), a high-content analysis microscope system was employed (IN Cell Analyzer 2000). FIGS. 6A and 6B summarize the results from automated cell counting in Hela and U2OS cells. In the case of Hela cells, approximately 50% of all the cells formed aggregates after expression of SS7-YFP (FIG. 6A). The baseline for YFP aggregation itself was around 10%. In the second aggregation-prone region, the mutation Y151E was found to completely abrogate the aggregation. Mutation M153K had no effect whatsoever on the aggregation rate, whereas mutant A154P gave very poor expression levels (and could not be quantified), suggesting that it interferes with the properties of the chromophore center. Mutations in the third aggregation-prone region, T225E and A227D, significantly reduced the aggregation rate to 35% and 38%, respectively, and when combined, to 30%. Combining single mutations from the second region with single mutations from the third region gave a significant reducing effect from 35% (mutants M153K/A227D and A154P/A227D) up to 44% (mutants M153K/T225E and A154P/T225E). For U2OS cells, similar observations were made as for HeLa cells. The highest reduction (>90%) in aggregation was observed for the Y151E mutant (FIG. 6B). The other mutations from the second aggregating region (M153K and A154P) had a very minor effect on the aggregation rate. The A227D mutation from the third region resulted in a significant decrease of the aggregation rate, which was even more pronounced when combined with the T225E mutant. Combining mutations from different regions for M153K/T225E and M153K/A227D gave the highest decrease to 45%. The strongest aggregation-reducing effect of the Y151E mutant in two different/independent cell lines suggests the universal nature of the SolubiS method.

Figure 6D:
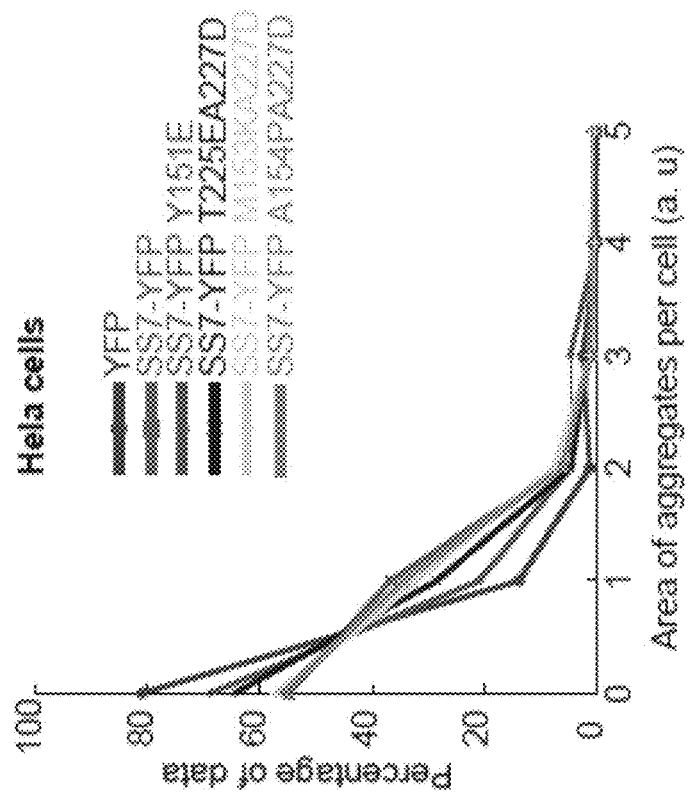
Figure 6C:
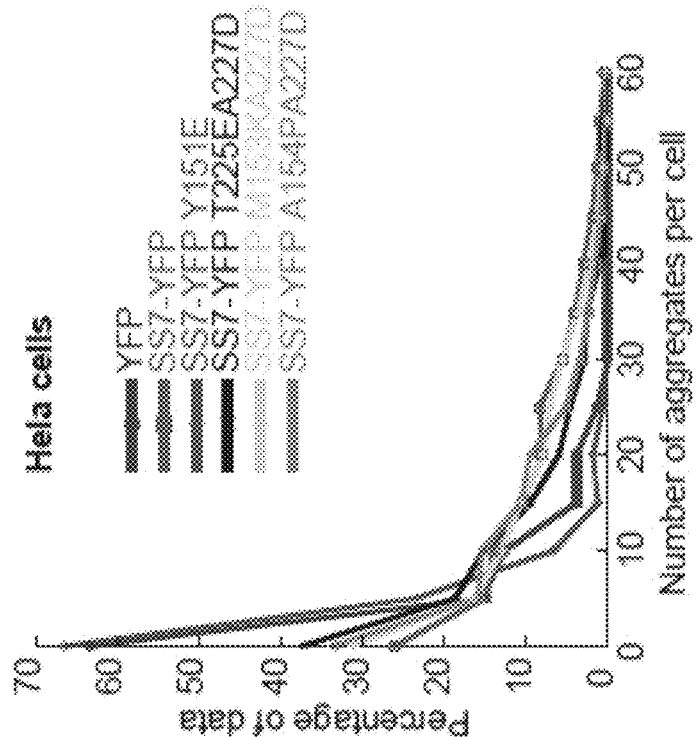
Figure 6F:
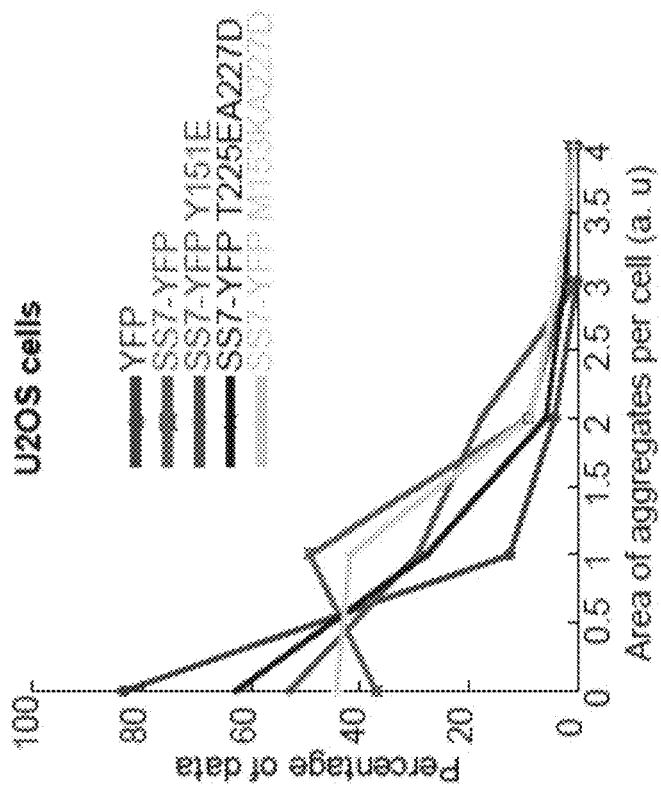
Figure 6E:
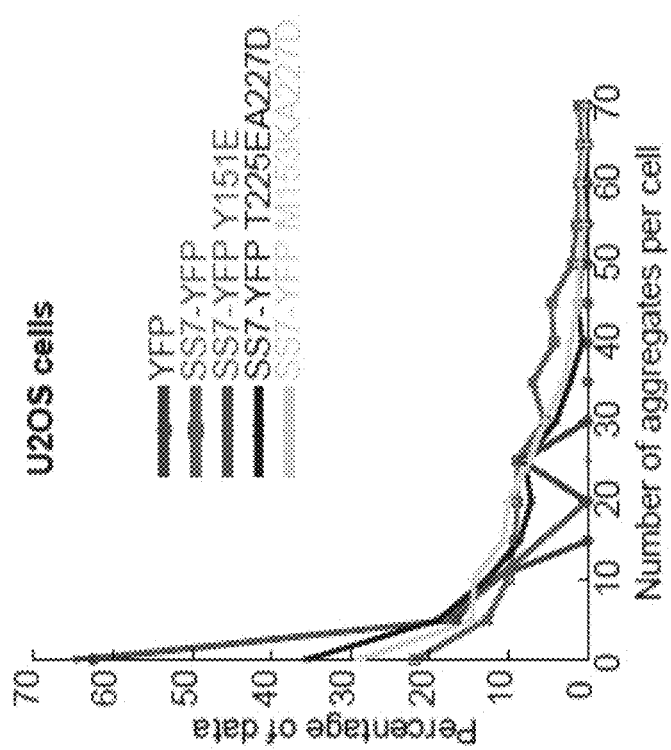

Looking at a number of the aggregates per cell, both in Hela (FIG. 6C) and U2OS (FIG. 6E), a decrease in the proportion of cells with high numbers of aggregates was observed for mutants Y151E, T225E/A227D and M153K/A227D in comparison to the model-aggregating protein SS7-YFP. Furthermore, there was a reduction of the total aggregates area per cell for mutants Y151E and T225E/A227D for both Hela (FIG. 6D) and U2OS cells (FIG. 6F).

Overall, these data demonstrate that extensive gatekeeper scans using TANGO, together with an assessment of the effect on thermodynamic stability by FoldX, allows identification of the structural features of a globular fold that are amenable to improvement.

4. Generation of a Less Aggregation Variant of the *Bacillus anthracis* Protective Antigen Anthrax infection caused by *Bacillus anthracis* may be classified based on the portal of entry into the host (cutaneous, gastrointestinal, or pulmonary), and symptoms may include fever with mild to severe systemic symptoms of malaise and headache. In severe forms of anthrax, general toxemia with shock, sepsis, and death may occur. The major virulence factor of *B. anthracis* consists of three proteins, edema factor, protective antigen (PA), and lethal factor (LF). The combination of PA and LF produces lethal toxin (LeTx) that is lethal in several animal models including mice. Recombinant PA (rPA) is currently being explored as a vaccine candidate but the protein suffers from poor stability and efficacy. Two aggregation-prone regions were identified in the PA protein (one in domain d3 and another one in domain d4). The sequence comprising the TANGO zone (underlined in NATNIYTVLDKIK (SEQ ID NO:4)) was based for the generation of a list of mutants. Mutant T605E was selected for introducing the compensatory mutation S588L for amino acid sequence numbering (see SEQ ID NO:3). Differential scanning calorimetry (DSC) shows in FIG. 8 that the mutant PA (S588L/T605E) only starts to aggregate at a higher temperature as compared to the wild-type PA.

In the next step, the in vitro biological activity of the mutant PA (S588L/T605E) was studied. Thereto, murine macrophage cells were treated with different concentrations of wild-type PA and mutant PA (S588L/T605E) in combination with lethal factor (for the macrophage toxicity assay, see B. Price et at (2001) *Infect. Immun.* 69:4509-4515). It was concluded that the biological activity of the mutant PA (S588L/T605E) is not only conserved but is also slightly improved as compared to the wild-type PA (see FIG. 9). Importantly, when the macrophage toxicity assay is carried out with wild-type and mutant PA (S588L/T605E), after a heat stress challenge at 45° C., the percentage of toxicity of mutant PA is preserved for a much longer time than the wild-type PA (see FIG. 10). In the next step, the effect of the protective effect of antisera derived from mice immunized with wild-type PA or mice immunized with mutant PA (S588L/T605E) was investigated. The data indicate that antisera derived from mice immunized with mutant PA (S588L/T605E) protect macrophages from toxicity when they are challenged with wild-type PA.

5. General Applicability of the SolubiS Method

Figure 7A:
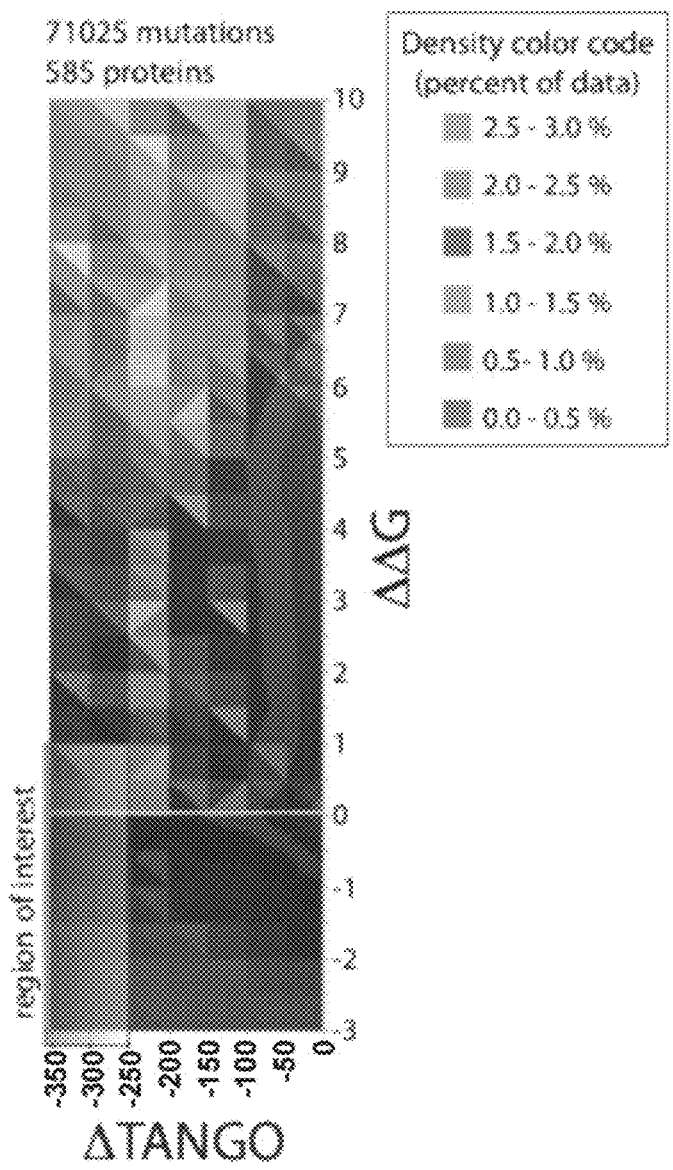
FIGS. 7A-7C: Results from SolubiS analysis run on selected protein structures.
Figure 7B:
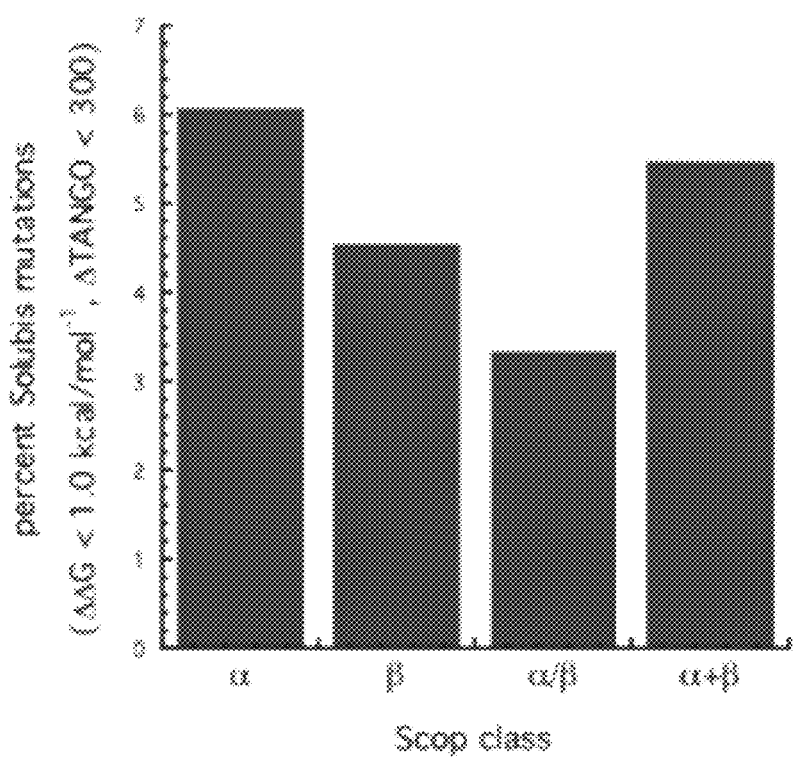
Figure 7C:
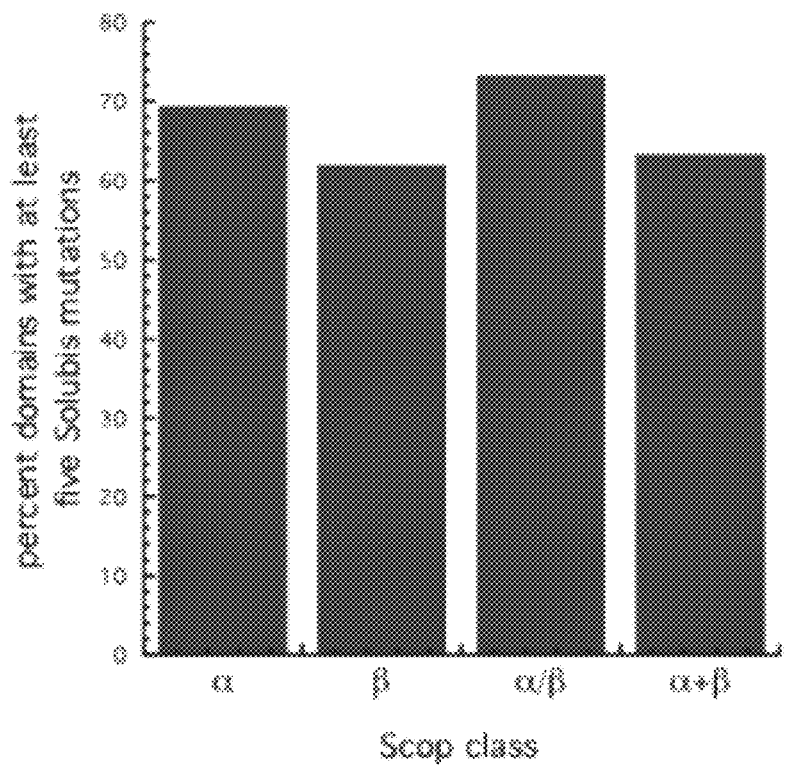

An obvious limitation of the method is the requirement of high resolution structural information, which, for human proteins, is available for 20-30% of the cases and is significantly lower for other species (Edwards 2009). If homology modeling is taken into account, the coverage could go up to 60-70% (Edwards 2009), albeit with a significant drop in accuracy on the ΔΔG calculation with FoldX. In order to investigate the applicability and scope of the SolubiS method, it was decided to run the analysis on a non-redundant set (sequence identity below 30%) of 585 protein domains for which high-quality structures are available (R-factor better than 0.19, resolution better than 1.5 A), which were selected by the WHATIF consortium (Hooft, Sander et al. 1996). For the current analysis, the structures were mapped to the SCOP structural classification of protein domains. In this set, the algorithm identified the aggregation-nucleating regions with TANGO and performed a systematic mutation screen to aggregation gatekeeper residues Arg, Lys, Pro, Asp and Glu of all amino acids belonging to an aggregating sequence (Rousseau, Serrano et al. 2006), and the resulting mutations were evaluated using both FoldX and TANGO. FIG. 7A shows a heat map version of the MASS plot for the >70,000 mutations generated for the 585 high-quality PDB structures in the current analysis in which the X-axis shows the change in TANGO score associated with the mutation, the Y-axis shows the ΔΔG score associated with the mutation, and the color code indicates the frequency of occurrence of mutations with that ΔTANGO and ΔΔG profile. The region of interest, i.e., mutations that maximally reduce aggregation while preserving thermodynamic stability, is indicated by a box (FIG. 7A), showing only a minority of mutants are fulfilling the SolubiS criteria. In FIG. 7B, the frequency of mutations that satisfy stringent SolubiS criteria (ΔΔG<1 kcal/mol and ΔTANGO<−300) is shown per structural class within SCOP ((α) all α-helical, (β) all β-sheet, (α/β) mixed α-helix and β-sheet, and (α+β) combined α-helix and β-sheet. The percentage of mutations identified using SolubiS is very similar for all SCOP classes and an average 4.5% of all gatekeeper mutations tested (71025). The scope of the method would be determined by the number of domains in which improving mutations could be found. Accepting some inaccuracy in the algorithms used, the following conservative statistic was employed: the percentage of domains was counted in which at least five candidate mutations could be identified that satisfy the aforementioned criteria, which makes it safe to assume that at least one of these will stand up to experimental validation (FIG. 7C). From the total of 585 analyzed proteins, 142 proteins do not carry a strong aggregating region and hence do not need to be improved. The analysis shows that, of the remaining 443 proteins, 49% of protein domains in the dataset are amenable to mutational improvement by SolubiS, with minor variations between the SCOP classes. When considering less rigorous criteria, so counting at least one SolubiS mutation per protein domain, 75% of them could be subjected to the redesign method.

Materials and Methods

1. In Silico Analysis of Aggregation, Stability and Structure of α-Galactosidase and YFP The aggregation propensities of α-Gal, YFP and their mutants were analyzed with TANGO (Fernandez-Escamilla, Rousseau et al. 2004), an algorithm to predict aggregation-nucleating sequences in proteins. The effect of the mutations on α-Gal and YFP stability was analyzed by calculating the change in free energy (ΔΔG) upon mutation with the FoldX forcefield (Schymkowitz, Borg et al. 2005). Structural changes of α-Gal and YFP due to mutations were analyzed with YASARA (Krieger, Koraimann et al. 2002).

2. Plasmid Construction and Mutagenesis

The full-length cDNA sequence encoding human α-Gal A (NM_000169) was cloned into the pcDNA4/TO/myc-His vector (Invitrogen). The insert was amplified using primers specific for the human α-Gal gene on Gene Pool cDNA template from human normal skeletal muscle (Invitrogen) with PHUSION® polymerase (Finnzymes). Then, the PCR product was digested with restriction enzymes HindIII and XhoI and cloned in pcDNA4/TO/myc-His vector to generate an open reading frame encoding α-Gal with a C-terminal Myc-tag. Expression vectors containing single, double and triple mutated α-Gal (D165V, A288D, A346P, A368P, A368R and S405L) were generated by site-directed mutagenesis using sequence-specific primers and PWO DNA polymerase (Roche).

YFP vector was kindly provided by Sam Lievens from VIB Department for Molecular Biomedical Research, UGent, Belgium. YFP model for aggregating proteins was established by adding to its N-terminal part the Hsp70 binding sequence (LLRLTGW (SEQ ID NO:5)) obtained from LIMBO algorithm. This sequence was cloned into pcDNA5/FRT/TO-Gateway-EYFP-FLAG vector using HindIII and KpnI restriction sites. Single and double mutations in YFP (Y151E, M153K, A154P, T225E and A227D) were introduced by site-directed mutagenesis using sequence-specific primers and PWO DNA polymerase (Roche).

3. Cell Culture and Transient Transfection

Human cervical cancer cell line HeLa and human osteosarcoma cell line U2OS (used for maximum 20 passages) were cultured in DMEM/F12 medium (Gibco) supplemented with 10% FCS and 1% antibiotics (penicillin/streptomycin) at 37° C. in 5% $CO_2$. For transient transfection in six-well culture plates, 350,000 of HeLa cells were plated per well in the medium without antibiotics. 1 μg of plasmid DNA was transfected into HeLa cells using FuGENE® HD transfection reagent (Roche) according to the manufacturer's protocol. For transient transfection in 96-well culture plates, 6,000 of HeLa and U2OS cells were plated per well in the medium without antibiotics. 0.1 μg of plasmid DNA was transfected into the cells using FuGENE® HD transfection reagent (Roche) according to the manufacturer's protocol. Forty-eight hours after transfection, cells were removed from the incubator and examined.

4. SDS-PAGE and Western Blot

Forty-eight hours after transfection, HeLa cells were lysed in RIPA buffer (1% octylphenoxypolyethoxyethanol (IGEPAL), 0.5% sodium deoxycholate and 0.1% sodium dodecyl sulfate (SDS)) (Pierce) supplemented with protease inhibitors (Roche) and fractionated by SDS-PAGE (Nu-PAGE® system, Invitrogen). For Western blot, the scraped cells were heated with 2% SDS buffer at 99° C. for 10 minutes, separated using a 10% Bis-Tris gel in MES running buffer and subsequently transferred by electroblotting (fixed current 0.4 A) on a nitrocellulose membrane (MILLIPORE®). The membrane was incubated in 5% dried non-fat milk powder dissolved in 0.2% Tris Buffer Saline TWEEN® (TBST) for one hour at room temperature (RT) and subsequently incubated with primary mouse anti-myc antibody (Invitrogen), followed by incubation by secondary goat HRP-conjugated anti-mouse IgG (Promega). Proteins were visualized using chemiluminescence immunoblotting detection reagent (ECL™, MILLIPORE®).

5. Size Exclusion Chromatography (SEC)

For the analysis of the α-Gal aggregation state by SEC, transfected HeLa cells were lysed in RIPA buffer supplemented with protease inhibitors, centrifuged 5 minutes at 3000 rpm and 400 μl of the supernatant was subsequently loaded onto a SUPERDEX® S200 HR10/30 column (GE Healthcare) equilibrated in hypotonic buffer (20 mM HEPES, 10 mM KCl, 1 mM $MgCl_2$, 1 mM EDTA, 1 mM EGTA, 1 mM DTT, pH 7.5). Eluted fractions were concentrated by 20% trichloroacetic acid precipitation, washed with acetone and analyzed by SDS-PAGE. The band densities were quantified using the QUANTITY ONE® program from the ChemiDoc System (Bio-Rad). A mixture of molecular weight markers (Bio-Rad) was injected onto the column as a gel filtration standard.

6. Enzymatic Assay

The activity of α-Gal was determined by fluorogenic substrate 4-methylumbelliferyl-α-D-galactopyranoside (5 mM 4-MU-α-Gal) as described previously (Mayes, Scheerer et al. 1981). N-acetylgalactosamine (D-GalNAc) was used as an inhibitor of α-Gal B activity. α-Gal B is a second α-Gal in the cells that hydrolyzes the artificial substrate but its activity in FD patients is normal or increased. In brief, HeLa cells transfected with wild-type or mutant α-Gal were harvested and lysed in PBS by three cycles of freezing/thawing in acetone-dry ice water bath. The supernatant obtained by centrifugation at 10,000×g was incubated with substrate solution (5 mM 4-MU-α-Gal and 100 mM D-GalNAc in 0.1 M citrate buffer pH 4.5) at 37° C. and the fluorescence was measured in a plate reader (POLARstar® OPTIMA, BMG Labtech) within an hour. The slope of the linear part of the substrate conversion curve was a measure of the concentration of active enzyme in the lysates. Additionally, α-Gal concentration in the whole cell lysates was determined by Western blot. To determine the enzymatic activity, the assays were performed in three independent experiments.

7. Analysis of the Aggregation of YFP Mutants

Hela and U2OS cells were transfected in a 96-well plate, as described above. Forty-eight hours after transfection, the cells were washed in Phosphate Buffer Saline pH 7.4 (PBS) and fixed with 4% formaldehyde (20 minutes, RT). Nuclei were stained with DAPI diluted 1:10,000 in PBS. In order to count the cells with aggregates, the IN Cell analyzer 2000 (GE Healthcare) was used, a high-content analysis system. Image acquisition was done using a 20× objective. For image analysis, the IN Cell Developer Toolbox (GE Healthcare) was employed.

8. Statistical Analysis

To confirm the consistency of the results, all described experiments were performed in a minimum of three separate replicates. For statistical evaluation of the determined averages and standard deviations of the mean, data were analyzed for significant differences using unpaired Student's t-test with a p-value less than 0.05 ($P<0.05$). Asterisks indicating the level of the p-value centered over the error bar mean: "*" p<0.05, "" p<0.01, "*" p<0.001 and "****" p<0.0001.

REFERENCES

Balch, W. E., R. I. Morimoto, et al. (2008). "Adapting proteostasis for disease intervention."*Science* 319(5865): 916-919.

Belli, M., M. Ramazzotti, et al. (2011). "Prediction of amyloid aggregation in vivo." *EMBO Rep.* 12(7):657-663.

Ben-Zvi, A., E. A. Miller, et al. (2009). "Collapse of proteostasis represents an early molecular event in *Caenorhabditis elegans* aging." *Proc. Natl. Acad. Sci. U.S.A.* 106(35):14914-14919.

Benichou, B., S. Goyal, et al. (2009). "A retrospective analysis of the potential impact of IgG antibodies to agalsidase beta on efficacy during enzyme replacement therapy for Fabry disease." *Mol. Genet. Metab.* 96(1):4-12.

Benjamin, E. R., R. Khanna, et al. (2012). "Co-administration With the Pharmacological Chaperone AT1001 Increases Recombinant Human alpha-Galactosidase A Tissue Uptake and Improves Substrate Reduction in Fabry Mice." *Mol. Ther.*

Bishop, N. A., T. Lu, et al. (2010). "Neural mechanisms of aging and cognitive decline."*Nature* 464(7288):529-535.

Brady, R. O., A. E. Gal, et al. (1967). "Enzymatic defect in Fabry's disease. Ceramidetrihexosidase deficiency." *N Engl. J. Med.* 276(21):1163-1167.

Chen, J. and B. Shen (2009). "Computational Analysis of Amino Acid Mutation: A Proteome Wide Perspective." *Current Proteomics* 6:228-234.

De Baets, G., J. Reumers, et al. (2011). "An evolutionary trade-off between protein turnover rate and protein aggregation favors a higher aggregation propensity in fast degrading proteins." *PLoS Comput. Biol.* 7(6):e1002090.

Dobson, C. M. (2004). "Principles of protein folding, misfolding and aggregation." Seminars in Cell & Amp; Developmental Biology 15(1):3-16.

Edwards, A. (2009). "Large-scale structural biology of the human proteome." *Annu. Rev. Biochem.* 78:541-568.

Eng, C. M., M. Banikazemi, et al. (2001). "A Phase ½ Clinical Trial of Enzyme Replacement in Fabry Disease: Pharmacokinetic, Substrate Clearance, and Safety Studies." *The American Journal of Human Genetics* 68(3): 711-722.

Eng, C. M. and R. J. Desnick (1994). "Molecular basis of Fabry disease: mutations and polymorphisms in the human alpha-galactosidase A gene." *Hum. Mutat.* 3(2): 103-111.

Fernandez-Escamilla, A. M., F. Rousseau, et al. (2004). "Prediction of sequence-dependent and mutational effects on the aggregation of peptides and proteins." *Nat. Biotechnol.* 22(10):1302-1306.

Futerman, A. H. and G. van Meer (2004). "The cell biology of lysosomal storage disorders."*Nat. Rev. Mol. Cell. Biol.* 5(7):554-565.

Griesbeck, O., G. S. Baird, et al. (2001). "Reducing the environmental sensitivity of yellow fluorescent protein. Mechanism and applications." *J. Biol. Chem.* 276(31): 29188-29194.

Hooft, R. W. W., C. Sander, et al. (1996). "Verification of protein structures: Side-chain planarity." *J. Appl. Cryst.* 29:714-716.

Ishii, S., R. Kase, et al. (1996). "Aggregation of the inactive form of human alpha-galactosidase in the endoplasmic reticulum." *Biochemical and Biophysical Research Communications* 220(3):812-815.

Kikis, E. A., T. Gidalevitz, et al. (2010). "Protein homeostasis in models of aging and age-related conformational disease." *Advances in Experimental Medicine and Biology* 694:138-159.

Krieger, E., G. Koraimann, et al. (2002). "Increasing the precision of comparative models with YASARA NOVA—a self-parameterizing force field." *Proteins* 47(3):393-402.

Lee, C. K., R. Weindruch, et al. (2000). "Gene-expression profile of the aging brain in mice." *Nat. Genet.* 25(3): 294-297.

Lieberman, R. L., A. D'Aquino J, et al. (2009). "Effects of pH and iminosugar pharmacological chaperones on lysosomal glycosidase structure and stability." *Biochemistry* 48(22):4816-4827.

Lu, T., Y. Pan, et al. (2004). "Gene regulation and DNA damage in the aging human brain." *Nature* 429(6994): 883-891.

Lund, J., P. Tedesco, et al. (2002). "Transcriptional profile of aging in *C. elegans.*" *Curr. Biol.* 12(18):1566-1573.

Mayes, J. S., J. B. Scheerer, et al. (1981). "Differential assay for lysosomal alpha-galactosidases in human tissues and its application to Fabry's disease." *Clinica chimica acta; International Journal of Clinical Chemistry* 112(2): 247-251.

Monsellier, E. and F. Chiti (2007). "Prevention of amyloid-like aggregation as a driving force of protein evolution." *EMBO Reports* 8(8):737-742.

Otzen, D. E., O. Kristensen, et al. (2000). "Designed protein tetramer zipped together with a hydrophobic Alzheimer homology: a structural clue to amyloid assembly." *Proc. Natl. Acad. Sci. U.S.A.* 97(18):9907-9912.

Park, J. S., K. Y. Han, et al. (2008). "Solubility enhancement of aggregation-prone heterologous proteins by fusion expression using stress-responsive *Escherichia coli* protein, RpoS." *BMC Biotechnol.* 8:15.

Pletcher, S. D., S. J. Macdonald, et al. (2002). "Genome-wide transcript profiles in aging and calorically restricted *Drosophila melanogaster.*" *Curr. Biol.* 12(9):712-723.

Porto, C., M. Cardone, et al. (2009). "The pharmacological chaperone N-butyldeoxynojirimycin enhances enzyme replacement therapy in Pompe disease fibroblasts." *Mol. Ther.* 17(6):964-971.

Richardson, J. S. and D. C. Richardson (2002). "Natural beta-sheet proteins use negative design to avoid edge-to-edge aggregation." *Proc. Natl. Acad. Sci. U.S.A.* 99(5): 2754-2759.

Rousseau, F., L. Serrano, et al. (2006). "How evolutionary pressure against protein aggregation shaped chaperone specificity." *J. Mol. Biol.* 355(5):1037-1047.

Schlieker, C., B. Bukau, et al. (2002). "Prevention and reversion of protein aggregation by molecular chaperones in the *E. coli* cytosol: implications for their applicability in biotechnology." *J. Biotechnol.* 96(1):13-21.

Schymkowitz, J., J. Borg, et al. (2005). "The FoldX web server: an online force field." *Nucleic Acids Res.* 33(Web Server issue): W382-388.

Shen, J. S., N. J. Edwards, et al. (2008). "Isofagomine increases lysosomal delivery of exogenous glucocerebrosidase." *Biochem. Biophys. Res. Commun.* 369(4):1071-1075.

Song, J. A., D. S. Lee, et al. (2011). "A novel *Escherichia coli* solubility enhancer protein for fusion expression of aggregation-prone heterologous proteins." *Enzyme Microb. Technol.* 49(2):124-130.

Soong, R., J. R. Brender, et al. (2009). "Association of highly compact type II diabetes related islet amyloid polypeptide intermediate species at physiological temperature revealed by diffusion NMR spectroscopy." *J. Am. Chem. Soc.* 131(20):7079-7085.

Tartaglia, G. G., S. Pechmann, et al. (2009). "A relationship between mRNA expression levels and protein solubility in *E. coli*." *J. Mol. Biol.* 388(2):381-389.

Tesmoingt, C., O. Lidove, et al. (2009). "Enzyme therapy in Fabry disease: severe adverse events associated with anti-agalsidase cross-reactive IgG antibodies." *Br. J. Clin. Pharmacol.* 68(5):765-769.

Thurberg, B. L., H. Rennke, et al. (2002). "Globotriaosylceramide accumulation in the Fabry kidney is cleared from multiple cell types after enzyme replacement therapy." *Kidney Int.* 62(6):1933-1946.

Van Dunne, J., S. Maurer-Stroh, et al. (2009). "Accurate prediction of DnaK-peptide binding via homology modelling and experimental data." *PLoS Comput. Biol.* 5(8): e1000475.

Wang, W. (1999). "Instability, stabilization, and formulation of liquid protein pharmaceuticals." *Int. J. Pharm.* 185(2): 129-188.

Xu, J., J. Reumers, et al. (2011). "Gain of function of mutant p53 by coaggregation with multiple tumor suppressors." *Nature Chemical Biology* 7(5):285-295.

Zhang, Y. B., J. Howitt, et al. (2004). "Protein aggregation during overexpression limited by peptide extensions with large net negative charge." *Protein Expr. Purif.* 36(2): 207-216.

Zou, S., S. Meadows, et al. (2000). "Genome-wide study of aging and oxidative stress response in *Drosophila melanogaster.*" *Proc. Natl. Acad. Sci. U.S.A.* 97(25):13726-13731.

The invention claimed is:

1. A method of producing a reduced aggregating variant of a wild-type protein, which wild-type protein has a high-resolution crystallographic structure available, the wild-type protein comprising at least two beta-aggregation regions, the method comprising:
   a) determining the at least two beta-aggregation regions in the wild-type protein;
   b) performing systematic mutation screens of aggregation gatekeeper residues R, K, E, D and P of all amino acids belonging to the determined beta-aggregation regions to generate a list of variant proteins thereof, wherein each variant protein thereof has at least one amino acid position in the at least two beta-aggregation regions changed to either R, K, E, D, or P;
   c) calculating, for each of the variant proteins, a predicted aggregation score and a predicted change in thermodynamic stability with respect to the wild-type protein; and
   d) producing, based upon the generated list, a reduced aggregating variant having, at the same time, a maximally reduced predicted aggregation and a maximal preservation of thermodynamic stability, so as to eliminate mutations from the list that thermodynamically destabilize the native structure with the use of an atomic force field.

2. A method of producing a reduced-aggregating variant of a wild-type protein, the wild-type protein having two or more beta-aggregation-regions and further having a high-resolution crystallographic structure available, the method comprising:
   conducting a systematic mutation screen of aggregation gatekeeper residues R, K, E, D and P of all amino acids belonging to a beta-aggregation region determined to be in the wild-type protein to identify variant proteins of the wild-type protein, wherein each variant protein identified has at least one amino acid position in the beta-aggregation region substituted with either R, K, E, D, or P;
   calculating, for each of the identified variant proteins, a predicted aggregation score and a predicted change in thermodynamic stability in comparison to the wild-type protein; and
   synthesizing a variant protein thus calculated to have both a maximally reduced predicted aggregation score and a maximal preservation of thermodynamic stability in comparison to the wild-type protein, so as to eliminate variant proteins that thermodynamically destabilize the wild-type protein's native structure with the use of an atomic force field.

* * * * *